(12) United States Patent
Rajavashisth

(10) Patent No.: US 7,247,618 B2
(45) Date of Patent: Jul. 24, 2007

(54) METHODS FOR INHIBITING MACROPHAGE COLONY STIMULATING FACTOR AND C-FMS-DEPENDENT CELL SIGNALING

(76) Inventor: Tripathi Rajavashisth, 15203 Florwood Ave., El Camino Village, CA (US) 90260

( * ) Notice: Subject to any disclaimer, the term of this patent is extended or adjusted under 35 U.S.C. 154(b) by 830 days.

(21) Appl. No.: 10/094,365

(22) Filed: Mar. 8, 2002

(65) Prior Publication Data

US 2002/0176847 A1    Nov. 28, 2002

Related U.S. Application Data

(60) Provisional application No. 60/287,426, filed on Apr. 30, 2001.

(51) Int. Cl.
| | |
|---|---|
| A61K 31/70 | (2006.01) |
| A01N 43/04 | (2006.01) |
| C07H 21/02 | (2006.01) |
| C07H 21/04 | (2006.01) |

(52) U.S. Cl. .................. 514/44; 536/23.1; 536/24.3; 536/24.33; 536/24.5
(58) Field of Classification Search .................. None
See application file for complete search history.

(56) References Cited

U.S. PATENT DOCUMENTS 5,019,381 A    5/1991    Garnick (Continued)

FOREIGN PATENT DOCUMENTS

WO    WO 01/30381    5/2001

OTHER PUBLICATIONS

Glass et al Atherosclerosis: The Road Ahead. Cell, 2001 vol. 104:503-516.*

(Continued)

*Primary Examiner*—Sean McGarry
*Assistant Examiner*—Terra C. Gibbs
(74) *Attorney, Agent, or Firm*—Seth D. Levy; Davis Wright Tremaine LLP

(57) ABSTRACT

Described herein are methods of inhibiting M-CSF activity, and, in particular, M-CSF/c-fms dependent cell signaling. In a first embodiment of the invention, one administers to a mammal viral vectors that deliver genes experessing antisense c-fms RNA; in a second embodiment, one induces in vivo production of a high-affinity soluble c-fms protein that competes for non-bound M-CSF; in a third embodiment, one administers a ribozyme-viral vector against c-fms mRNA; and in a fourth embodiment, one administers oligodeoxynucleotides that inhibit expression of c-fms gene product. The methods may be used to treat any disease in which M-CSF activity plays a role, and are particularly effective in treating and preventing atherosclerosis.

Embodiments of the present invention are directed primarily, but not exclusively, to a method for treating and preventing cardiovascular disease by inhibiting receptors to M-CSF. Other embodiments of the present invention include any and all biologic and/or pathobiologic phenomena mediated in whole or in part by M-CSF signaling through its receptor. Pathobiologic phenomena include, but are not limited to, disease entities such as osteoporosis, Alzheimer's disease, diabetes mellitus (Type 1 and/or Type 2), infectious diseases, cancer, and inherited disorders characterized by defects in one or more components in the M-CSF signaling pathway.

11 Claims, 19 Drawing Sheets
(7 of 19 Drawing Sheet(s) Filed in Color)

U.S. PATENT DOCUMENTS

| | | | |
|---|---|---|---|
| 5,021,239 A | 6/1991 | Garnick |
| 5,084,556 A | 1/1992 | Brown |
| 5,087,453 A | 2/1992 | Strassmann |
| 5,112,961 A | 5/1992 | Hayashida et al. |
| 5,186,931 A | 2/1993 | Kishimoto et al. |
| 5,211,947 A | 5/1993 | Brannan et al. |
| 5,288,487 A | 2/1994 | Kawashima et al. |
| 5,290,549 A | 3/1994 | Garnick |
| 5,340,573 A | 8/1994 | Garnick |
| 5,475,087 A | 12/1995 | Seelig et al. |
| 5,629,283 A | 5/1997 | Nicola et al. |
| 5,635,388 A | 6/1997 | Bennett et al. |
| 5,650,299 A | 7/1997 | Lawman et al. |
| 5,658,756 A | 8/1997 | Rodan et al. |
| 5,705,611 A | 1/1998 | Hayashida et al. |
| 5,714,140 A | 2/1998 | Strassmann |
| 5,726,036 A | 3/1998 | Nicola et al. |
| 5,734,039 A | 3/1998 | Calabretta et al. |
| 5,747,032 A | 5/1998 | Metcalf et al. |
| 5,811,301 A | 9/1998 | Cameron |
| 5,814,479 A | 9/1998 | Zhou et al. |
| 5,830,760 A | 11/1998 | Tsai et al. |
| 5,849,283 A | 12/1998 | Ciliberto et al. |
| 5,851,829 A | 12/1998 | Marasco et al. |
| 5,866,114 A | 2/1999 | Pandit et al. |
| 5,866,397 A | 2/1999 | Rodan et al. |
| 5,874,546 A | 2/1999 | Nagata et al. |
| 5,888,495 A | 3/1999 | Schrier et al. |
| 5,891,432 A | 4/1999 | Hoo |
| 5,914,106 A | 6/1999 | Ciliberto et al. |
| 5,939,063 A | 8/1999 | Vadas et al. |
| 5,965,371 A | 10/1999 | Marasco et al. |
| 5,981,708 A | 11/1999 | Lawman et al. |
| 5,985,265 A | 11/1999 | Kinstler et al. |
| 5,997,865 A | 12/1999 | Bennett et al. |
| 6,004,940 A | 12/1999 | Marasco et al. |
| 6,025,146 A | 2/2000 | Pandit et al. |
| 6,033,856 A | 3/2000 | Koerner et al. |
| 6,046,047 A | 4/2000 | Crabtree et al. |
| 6,072,036 A | 6/2000 | Marasco et al. |
| 6,080,575 A | 6/2000 | Heidtmann et al. |
| 6,100,070 A | 8/2000 | Zurfluh et al. |
| 6,136,957 A | 10/2000 | Nicola et al. |

OTHER PUBLICATIONS

Branch, A. A Good Antisense is Hard to Find. TIBS, Feb. 1998 vol. 23, pp. 45-50.*

Jen et al. Suppression of Gene Expression by Targeted Disruption of Messenger RNA: Available Options and Current Strategies. Stem Cells, 2000, vol. 18:307-319.*

Yokoyama et al. Modulation of c-fms proto-oncogene in an ovarian carcinoma cell line by a hammerhead ribozyme. British Journal of Cancer, 1997 vol. 76:977-982.*

Sansilvestri et al. Blood, 1995 vol. 86, No. 5, pp. 1729-1735. Early CD34 high Cells Can Be Separated into KIT high Cells in which Transforming Growth Factor-beta (TGF-beta) Downmodulates c-kit and KIT low Cells in which Anti-TGF-beta Upmodulates c-kit.*

P. Smaglik, "Making Sense of Antisense," *The Scientist*, vol. 12[17]:1 (Aug. 1998).

A. D. Branch, "Letter: Making Sense of Antisense," *The Scientist*, vol. 12[20]: 8 (Oct. 1998).

"Antisense Drug Against Lymphoma," *Academic Press Daily inScight*, http://www.apnet.com/inscight/04171997/grapha.htm (Apr. 18, 1997).

Borycki, Anne-Gaelle, "Colony-Stimulating Factor 1 (CSF-1) Is Involved in an Autocrine Growth Control of Rat Myogenic Cells," *Experimental Cell Research*, vol. 218, pp. 213-222 (1995).

Himes et al., "A highly conserved c-*fms* gene intronic element controls macrophage-specific and regulated expression," *Journal of Leukocyte Biology*, vol. 70, pp. 812-820 (Nov. 2001).

Bocycki, Anne-Gaelle et al., "Repression of the CSF-1 receptor (c-*fms* proto-oncogene product) by antisense transfection induces G1-growth arrest in L6x1 rat myoblasts," *Oncogene*, vol. 10, pp. 1799-1811 (1995).

Y. Yokoyama et al., "Modulation of c-*fms* proto-oncogene in an ovarian carcinoma cell line by a hammerhead ribozyme," *British Journal of Cancer*, vol. 76(8), pp. 977-982 (1997).

Sansilvestri, Patricia et al., Early $CD34^{high}$ Cells Can Be Separated Into $KIT^{high}$ Cells in Which Transforming Growth Factor-$\beta$ (TGF-$\beta$) Downmodulates c-*kit* and $KIT^{low}$ Cells in Which Anti-TGF-$\beta$ Upmodulates c-*kit*.

Birchenall-Roberts, Maria C. et al., "Inhibition of Murine Monocyte Proliferation by a Colony-Stimulating Factor-1 Antisense Oligodeoxynucleotide," *The Journal of Immunology*, vol. 145, pp. 3290-3296 (Nov. 15, 1990).

T. Inaba and N. Yamada, "Involvement of Transcription Factor PU.1 in Phenotypic Transformation of Vascular Smooth Muscle Cells to Macrophage-like Cells," *Third Department of Internal Medicine* (*University of Tokyo*), vol. 24, No. 4-5 (1996).

J. Wu et al., "The role of the c-*fms* oncogene in the regulation of HL-60 cell differentiation," *Oncogene*, vol. 5, pp. 873-877 (1990).

T. Inaba et al., "Transcription Factor PU.1 Mediates Induction of c-*fms* in Vascular Smooth Muscle Cells: a Mechanism for Phenotypic Change to Phagocytic Cells," *Molecular and Cellular Biology*, vol. 16, No. 5, pp. 2264-2273 (May 1996).

Herembert, T. et al., *Control of Vascular Smooth-Muscle Cell Growth by Macrophage-Colony-Stimulating Factor*, Biochemical Journal, 325(1):123-128 (1997).

Pavlides G. S. et al., *Intramural Drug Delivery by Direct Injection Within the Arterial Wall : First Clinical Experience With a Novel Intracoronary Delivery-Infiltrator System*, Catheterization and Cardiovascular Diagnosis, 41(3):287-292 (Jul. 1997).

Rajavashisth, T. et al., *Heterozygous Osteopetrotic (op) Mutation Reduces Atherosclerosis in LDL Receptor-deficient Mice*, Journal of Clinical Investigation, 101(12):2702-2710 (Jun. 15, 1998).

Rajavashisth, T. et al., *Local Adenoviral Delivery of Antisense c-fms Gene Inhibits In-Stent Stenosis in Porcine Coronary Arteries*, Circulation, 108(17):IV-6 (Oct. 28, 2003) Supplement.

* cited by examiner

| PFU/ml | MTT Absorbance | |
|---|---|---|
| | Ad5CMVpolyA | Ad5CMVc-fmsAS |
| 0 | 1.296 | 1.857 |
| 10 | 1.318 | 2.073 |
| $10^2$ | 1.113 | 1.716 |
| $10^3$ | 1.036 | 1.272 |
| $10^4$ | 1.085 | 0.720 |
| $10^5$ | 1.287 | 0.671 |

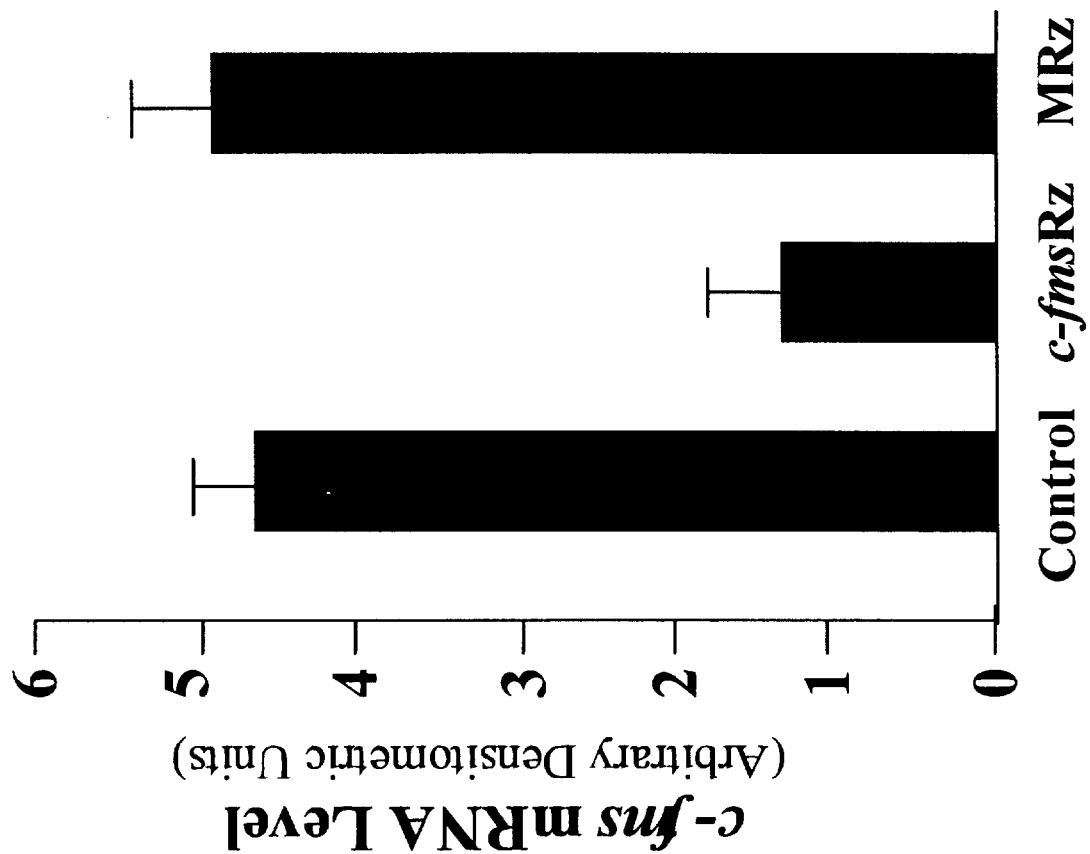

METHODS FOR INHIBITING MACROPHAGE COLONY STIMULATING FACTOR AND C-FMS-DEPENDENT CELL SIGNALING

This application claims the benefit of priority under 35 U.S.C. § 119 of provisional U.S. application Ser. No. 60/287,426, filed Apr. 30, 2001, the contents of which are hereby incorporated by reference.

FIELD OF THE INVENTION

Embodiments of the present invention are directed to inhibiting macrophage-colony stimulating factor (M-CSF) cell signaling—and, in particular, the diseases caused by such signaling—by inhibiting or otherwise interfering with the expression and/or biological activity of the M-CSF receptor, the product of the proto-oncogene c-fms.

BACKGROUND OF THE INVENTION

Macrophage colony stimulating factor plays an important role in many biological processes, including the development of blood cells and the regulation of the immune system. It also plays an important role in atherosclerosis, osteoporosis, and other diseases. Its role in atherosclerosis is the most significant because, if anything, this disease is the leading cause of death in most developed countries.

Atherosclerosis is an inflammatory process of the arteries that begins as a fatty deposit (primarily lipid-filled macrophages), progresses to a fibrofatty lesion (all the foregoing, plus a mesh of smooth muscle cells, T-cells, collagen, proteoglycans, and elastic fibers), and ultimately leads to a fibrous plaque (all the foregoing, plus dense connective tissue and necrotic debris). If a person fails to treat the plaque or modify the diet or other lifestyle characteristics that likely contributed to it, the lesion will eventually occlude most or all of the artery, and the person will experience symptoms of heart disease such as chest pain, may have a heart attack, and might even die. Even if he escapes a heart attack, he is still vulnerable to stroke, gangrene of the extremities, damage to internal organs, and other serious diseases. As a result, atherosclerosis is the single most important cause of death and disability in developed countries in America, Europe and Asia, and will soon overtake infection as the primary cause of death in the entire world (R. Ross, "The Biology of Atherosclerosis," in E. Topol, Ed., *Comprehensive Cardiovascular Medicine*, Lippincott-Raven, Philadelphia (1998); C J L Murray, A D Lopez. Mortality by cause for eight regions of the world: Global Burden of Disease Study. Lancet. 349:1269–1276 (1997); T. A. Pearson, S. C. Smith, P. Poole-Wilson, "Cardiovascular specialty societies and the emerging global burden of cardiovascular disease: a call to action," *Circulation*. 97:602–604 (1998).

Widely accepted scientific opinion maintains that atherosclerosis is a complex inflammatory response to injury of the blood vessel, and a crucial early event in atherosclerosis is injury of some form to the arterial endothelium. Oxidized low-density lipoprotein (Ox-LDL) is a major source of injury; toxins, viruses, homocystein, and mechanical injury are other sources. The interaction of these agents with the endothelium changes the endothelial cells, making them prone to further interaction with monocytes circulating in the blood. Injury to the endothelium permits monocytes and other inflammatory cell types to penetrate the outer layer of the endothelium, where they differentiate into macrophages. Macrophages proliferate within the developing lesion and load themselves with Ox-LDL and acquire a foamy appearance. The lipids activate the macrophages, which then express new genes for stimulating smooth muscle cells, producing enzymes, and stimulating other macrophages, all of which make a major contribution to the development of the atherosclerotic plaque. If injury to the endothelium continues, the smooth muscle cells migrate and proliferate into the subendothelial space and combine with connective tissue and other matter, thereby forming an atherosclerotic lesion. The developing lesion begins to occupy more and more volume, and eventually encroaches upon the inside of the blood vessel, thereby restricting the flow of blood, and frequently blocking the artery altogether.

The most effective known method to treat atherosclerosis is to modify, where possible, the risk factors associated with it (some risk factors, such as gender, cannot be modified). Proper exercise and diet, maintaining a healthy weight, drinking in moderation, and not smoking can significantly reduce atherosclerosis and the diseases (e.g., heart attack, stroke) it causes. This is easier said than done, of course: the prevalence of atherosclerosis suggests that most individuals have difficulty making the sacrifices that proper exercise and diet require or that they succumb to the disease nonetheless. The most common pharmacological treatment for atherosclerosis seeks to lower blood levels of LDL, the so-called "bad cholesterol." This method of treatment is effective in reducing the complications of atherosclerosis in many individuals, yet it is not a cure: atherosclerosis remains a leading cause of death and disability. For these reasons, a basic medical text still teaches that "[t]reatment of established atherosclerosis is directed at its complications . . ." M. H. Beers and R. Berkow, eds., *Merck Manual of Diagnosis and Therapy*, 1658 (1999).

However, if it were possible to disrupt, at the cellular level, the process that causes atherosclerosis, one could direct treatment at the disease itself, instead of its complications. For example, if there were a method to inhibit the growth, survival or activation of macrophages (or of vascular smooth muscle cells that feature prominently in the diseased artery wall), one might be able to prevent the formation and progression of atherosclerosis, and this would obviously be far preferable to merely treating its complications. The present invention is directed to such a method.

Over the years, the inventor and his colleagues have accumulated evidence which strongly indicate that M-CSF/c-fms-dependent cell signaling contributes to both the development and the breakdown of atherosclerotic lesions by regulating the growth, survival and function of monocyte-macrophages and intimal smooth muscle cells. T. B. Rajavashisth et al., "Induction of endothelial cell expression of granulocyte and macrophage colony-stimulating factors by modified LDL," *Nature*, 344:254–257 (1990); T. B. Rajavashisth et al., "Transcriptional activation of the macrophage-colony stimulating factor gene by minimally modified LDL: involvement of nuclear factor KB," *Arterioscler Thromb Vasc Biol.*, 15:1591–1598 (1995); T. B. Rajavashisth et al, "Transcriptional activation of the macrophage-colony stimulating factor gene by minimally modified LDL: involvement of nuclear factor kB," *Arterioscler Thromb Vasc Biol*, 15:1591–1598 (1995); T. B. Rajavashisth et al., "Atherosclerosis: from risk factors to regulatory molecules," in *Encyclopedia of Human Biology*, R. Delbacco and P. Abelson, eds. Academic Press, San Diego, Calif., 1:565–574 (1997). They have established this conclusion in vivo by studying atherogenesis in osteopetrotic (op) mice that lack M-CSF due to a point mutation in the M-CSF gene. Atherogenesis was induced either by feeding the mice a high fat, high cholesterol diet or by crossing op mice with either apolipoprotein (apo) E or LDL receptor (LDLR)-null mice to generate mice lacking both M-CSF and apo E or LDLR. J. H. Qiao et al., "Role of macrophage-colony stimulating factor in atherosclerosis: studies of osteopetrotic mice," *Am J Pathol*, 150:1687–1699 (1997); T. B. Rajavashisth et al., "Heterozygous osteopetrotic (op) mutation reduces atherosclerosis in LDL receptor deficient mice," *J Clin Invest*, 101: 2702–2710 (1998). The absence of M-CSF in both apo E or LDLR-deficient mice results in decreased atherosclerosis despite marked hypercholesterolemia suggesting that inhibition of M-CSF function in the diseased vessel wall may confer antiatherogenic properties.

An early event in the development of atherosclerotic lesion also includes migration of SMC from the media to the intima of the artery wall, where they proliferate and load themselves with lipid and thus become foam cells. J. Thyberg et al., "Regulation of differentiated properties and proliferation of arterial smooth muscle cells," *Arteriosclerosis*, 10:966–990 (1990); R. Ross, "The platelet-derived growth factor," *Cell*, 46:155–169 (1986). Numerous observations suggest that during the atherogenic process SMC change their structure and function. ld. Although the precise mechanism of this phenotypic modulation remains unclear, several growth factors or cytokines appear to play an important role in this process. Intimal SMC derived from atherosclerotic lesions express increased levels of M-CSF isoforms and its receptor, c-fms. R. Ross et al., "Localization of PDGF-B protein in macrophages in all phases of atherogenesis," *Science*, 248:1009–1012 (1990); R. N. Salomon et al., "Increased apolipoprotein E and c-fms gene expression without elevated interleukin 1 or 6 mRNA levels indicates selective activation of macrophage functions in advanced human atheroma," *Proc Natl Acad Sci USA*, 89:2814–2818 (1992). SMC can express c-fms when activated by cytokines such as platelet-derived growth factor (PDGF), transforming growth factor-β (TGF-β), heparin-binding epidermal growth factor-like growth factor (HB-EGF), or phorbol esters. T. Inaba et al., "PDGF induces c-fms and scavenger receptor genes in vascular smooth muscle cells," *J Biol Chem.*, 267:17107–13112 (1992); T. Inaba et al., "Induction of sustained expression of proto-oncogene c-fms by platelet-derived growth factor, epidermal growth factor, and basic fibroblast growth factor, and its suppression by interferon-gamma," *J Clin Invest*, 95:1133–1139 (1995); T. Inaba et al., "Synergistic effects of transforming growth factor β on the expression of c-fms, macrophage colony-stimulating factor receptor gene, in vascular smooth muscle cells," *FEBS Left*, 399:207–210 (1996). These results imply that activated SMC may respond mitogenically to M-CSF, a possibility with important implications for atherogenesis; that is, since M-CSF expression is increased in atherosclerotic lesions compared to the normal artery, M-CSF may play an important role in mitogenically altering SMC, and cause them to contribute to the further development of atherosclerotic lesions.

To examine the role of M-CSF in proliferation of arterial SMC, the inventor has previously used cultured human aortic SMC (HASMC) as a primary cell model and the injured rat carotid artery as an in vivo model. T. Rajavashisth et al., "Role of induced expression of M-CSF and its receptor in the growth and proliferation of intimal smooth muscle cells," *Circulation*, 88:1–468 (1993). His results indicate that induced expression of M-CSF and c-fms correlates strongly with the initiation of SMC proliferation observed in balloon-injured rat carotid artery. Intimal SMC express higher levels of M-CSF receptor as compared to medial SMC and proliferate in response to M-CSF, thus providing indirect evidence that induced M-CSF activity not only affects monocyte-macrophage proliferation but can also affect the proliferation of intimal SMC; this suggests a broader role for M-CSF in atherosclerosis. These findings are supported by observations in osteopetrotic (op) mice that totally lack M-CSF. In a periadventitial carotid arterial injury model in the op/op mouse, M-CSF deficiency markedly inhibits injury-induced intimal thickening and neointimal proliferation. Additionally, results from the effects of purified M-CSF on the growth of cultured HASMC favor the concept that intimal SMC acquire certain characteristics of monocyte-macrophages that may be related to their proliferation and phenotypic conversion into foam cells in atherosclerotic lesions. Recent studies from other investigators support the inventor's finding that M-CSF can modulate the growth of vascular SMC. T. Inaba et al., "Transcription factor PU.1 mediates induction of c-fms in vascular smooth muscle cells: A mechanism for phenotypic change to phagocytic cells," *Mol Cell Biol*, 16:2264–2273 (1996); T. Herembert et al., "Control of vascular smooth-muscle cell growth by macrophage-colony-stimulating factor," *Biochem J*, 325:123–128 (1997).

M-CSF is a multifunctional protein that can stimulate the growth of monocyte-macrophages, trophoblasts, osteoclasts and vascular SMC and is necessary for the survival of these cells in culture and in vivo. E. R. Stanley et al., "CSF-1: a mononuclear phagocyte lineage specific hemopoetic growth factor," J Cell Biochem, 21:151-159 (1983); R. J. Tushinski et al., "Survival of mononuclear phagocytes depends on a lineage-specific growth factor that the differentiated cell selectively destroy," *Cell*, 28:71–77 (1982). Vessel wall bound M-CSF, in particular, can regulate recruitment, cell cycle, survival and proliferation of monocyte-macrophages leading to the genesis and progression of atheromatous lesions. The ability of M-CSF to stimulate the uptake and degradation of modified lipoproteins by upregulating scavenger receptors may lead to the removal of oxidized lipoproteins from the extracellular space and the generation of foam cells. S. Ishibashi, "Monocyte colony-stimulating factor enhances uptake and degradation of acetylated low-density lipoproteins and cholesterol esterification in human monocyte-derived macrophages," *J Biol Chem*, 265:14109–14117 (1990); W. J. S. de Villiers et al., "Macrophage-colony stimulating factor selectively enhances macrophage scavenger receptor expression and function," *J Exp Med*, 80:705–709 (1994); H. Shimano, "Human monocyte CSF enhances the clearance of lipoproteins containing apolipoprotein B-100 via both low-density lipoprotein receptor-dependent and -independent pathways in rabbits," *J Biol Chem*, 265:12869–12875 (1990).

M-CSF exists in multiple isoforms. A single M-CSF gene gives rise to at least four distinct mRNAs due to alternative splicing in mice and humans. Rajavashisth et al., "Cloning and tissue-specific expression of mouse colony-stimulating factor mRNA," Proc Natl Acad Sci USA, 84:1157–1161 (1987); D. P. Cerretti et al., "Human macrophage-CSF: alternative RNA and protein processing from a single gene," *Mol Immunol*, 25:761–770 (1988). In mice, various tissues express a complex pattern of multiple M-CSF transcripts (ranging from 1.6 to 4.5 kb) in a highly tissue specific manner. These transcripts encode at least two distinct proteins, secreted as glycoprotein (sM-CSF) and proteoglycan (pgM-CSF) forms, and a third membrane bound (mM-CSF) isoform with cell-surface biological activity. M. B. Ladner et al., "Human CSF-1: Gene structure and alternative splicing of mRNA precursors," *EMBO J.*, 6:2693–2698 (1987); D. P. Cerretti et al., "Human macrophage-CSF: alternative RNA and protein processing from a single gene," *Mol Immunol*, 25:761–770 (1988); E. S. Kawasaki et al., "Molecular cloning of a complementary DNA encoding human macrophage-specific colony stimulating factor (CSF-1)," *Science*, 230:291–296 (1985); S. Suzu et al., "Identification of a high molecular weight macrophage colony-stimulating factor as a glycosaminoglycan-containing species," *J Biol Chem*, 267:4345–4348 (1992); C. W. Rettenmier et al., "Synthesis of membrane-bound colony-stimulating factor 1 (CSF-1) and down modulation of CSF-1 receptors in NIH3T3 cells transformed by cotransfection of the human CSF-1 and c-fms," *Mol Cell Biol*, 8:2378–2387 (1987). Precursors of mature M-CSF isoforms contain a common amino terminus, a spacer region of varying length, and a common trans-membrane domain at the carboxy terminus. The membrane bound precursor may be processed by different proteolytic activities located at different sites in the body, producing the secreted isoform of M-CSF. It is also possible that membrane bound M-CSF molecules function as cell-associated ligands stimulating biological response in a "juxtacrine" manner (i.e., requiring cell to cell contact). In this respect, the three different M-CSF isoforms would in effect extend the ligand binding domain of the amino terminus from the membrane, and thus allow a cell to stimulate a c-fms receptor on another cell located at a variable distance from the cell initiating the M-CSF signal.

Multiple isoforms of M-CSF utilize a single membrane bound receptor (c-fms), C. J. Sherr et al., "Macrophage colony-stimulating factor, CSF-1, and its proto-oncogene-encoded receptor," *Cold Spring Harbor Symp Quant Biol*, 53:521–530 (1988), suggesting that this receptor may be a suitable target to inhibit M-CSF mediated cell signaling. This idea is directly supported by evidence indicating that systemic injection of a monoclonal antibody against murine c-fms in the LDLR-deficient mice results in markedly reduced atherosclerosis. T. B. Rajavashisth et al., "Monoclonal antibody against murine macrophage colony-stimulating factor receptor inhibits atherogenesis in LDL receptor-deficient mice," *Circulation* 98:A1711,1198. These studies demonstrate that the monoclonal antibody specific to the ligand binding domain of the M-CSF receptor markedly inhibits atherosclerosis in LDLR-deficient mice. Furthermore, these studies strongly support the concept that M-CSF plays a key role in the genesis and progression of atherosclerosis. Although the exact mechanism by which anti-c-fms antibody confers its resistance to atherosclerosis remains to be elucidated, the observation that the disruption of M-CSF/c-fms signaling pathways inhibits atherosclerosis suggests that therapy based on disruption of M-CSF/c-fms signaling pathways could have potential as an effective antiatherogenic strategy.

Although anti-c-fms antibody inhibits atherosclerosis in mice, treating atherosclerosis (or any other disease in which inhibiting M-CSF would have a beneficial effect) by administering this antibody is not practical in humans. Producing such antibodies is expensive. It demands much laboratory time and many laboratory resources. To effectively administer it, one would need to deliver frequent intravenous injections to patients, which further limits its usefulness. There is therefore a need in the art for a method of inhibiting M-CSF, and, in particular, M-CSF/c-fms cell signaling, that does not depend on administering anti-c-fms antibodies; this arises from the even greater need for a method of treating atherosclerosis itself—the leading cause of death in much of the world—and not merely its complications. The inventor is the first to describe such a method, as set forth herein.

SUMMARY OF THE INVENTION

The present invention is directed to methods of disrupting the biological effects of M-CSF by inhibiting the expression and/or function of its membrane bound receptor, c-fms. These methods permit one to treat any disease in which inhibiting M-CSF would have a beneficial effect.

A first embodiment of the present invention is directed to a method of inhibiting M-CSF/c-fms cell signaling by administering to a mammal recombinant viral vectors (e.g., adenovirus, adeno-associated virus, retroviruses, lentiviruses, or other viral vectors) that deliver genes expressing antisense c-fms RNA; doing so inhibits the expression of c-fms, thereby inhibiting M-CSF/c-fms cell signaling. An optimal amount of viral particles and an effective and convenient route to administer it (e.g., by administering it intravenously or intramuscularly) can readily be determined by one of ordinary skill in the art of microbiology.

A second embodiment of the present invention is directed to a method of inhibiting M-CSF/c-fms cell signaling by inducing in vivo production of a high affinity soluble c-fms protein that competes for non-bound M-CSF but lacks all of its signal transduction domain. The method involves delivering viral vectors to produce an amount of soluble c-fms (or its derivative) that is sufficient to reduce the amount of M-CSF ligand and thereby inhibit the M-CSF/c-fms cell signaling pathway.

A third embodiment of the present invention is directed to a method of inhibiting M-CSF/c-fms cell signaling with somatic-cell gene therapy. According to this method, one administers a ribozyme-viral (adeno, adeno-associated, lentiviral or other) vector against c-fms mRNA in a mammal. The method utilizes a hammerhead ribozyme expression cassette in a viral backbone that targets the GUC sequence in codon 18 of c-fms mRNA. Ribozymes have sequence-specific endoribonuclease activity, which makes them useful for sequence-specific cleavage of mRNAs and further inhibition of gene expression. Ribozyme therapy is widely regarded as a new and potential pharmaceutical class of reagent to treat a number of medical disorders. A desired quantity or the length of expression of the ribozyme-viral vector can be readily determined without undue experimentation, as can the most effective and convenient route of administering it. Ribozyme-viral vectors against c-fms mRNA permit one to uniquely assess the contribution of M-CSF mediated cell signaling to vascular physiology, and to therapeutically intervene in the pathology such signaling causes.

A fourth embodiment of the present invention provides a non-viral method to inhibit the expression of c-fms. This method involves antisense therapy using oligodeoxynucleotides (ODN) that inhibit the expression of the c-fms gene product by specific base pairing of single stranded regions of the c-fms mRNA. The method involves synthesis of ODN complememtary to the first 15 nucleotides of c-fms mRNA starting with the initiation codon AUG; this codon is optimized for uptake and stability by cultured mouse bone-marrow derived macrophages and vascular smooth muscle cells. The method further provides an effective amount of ODN to inhibit the M-CSF/c-fms dependent cell signaling pathways in a mammal.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

DETAILED DESCRIPTION OF THE INVENTION

Figure 1:
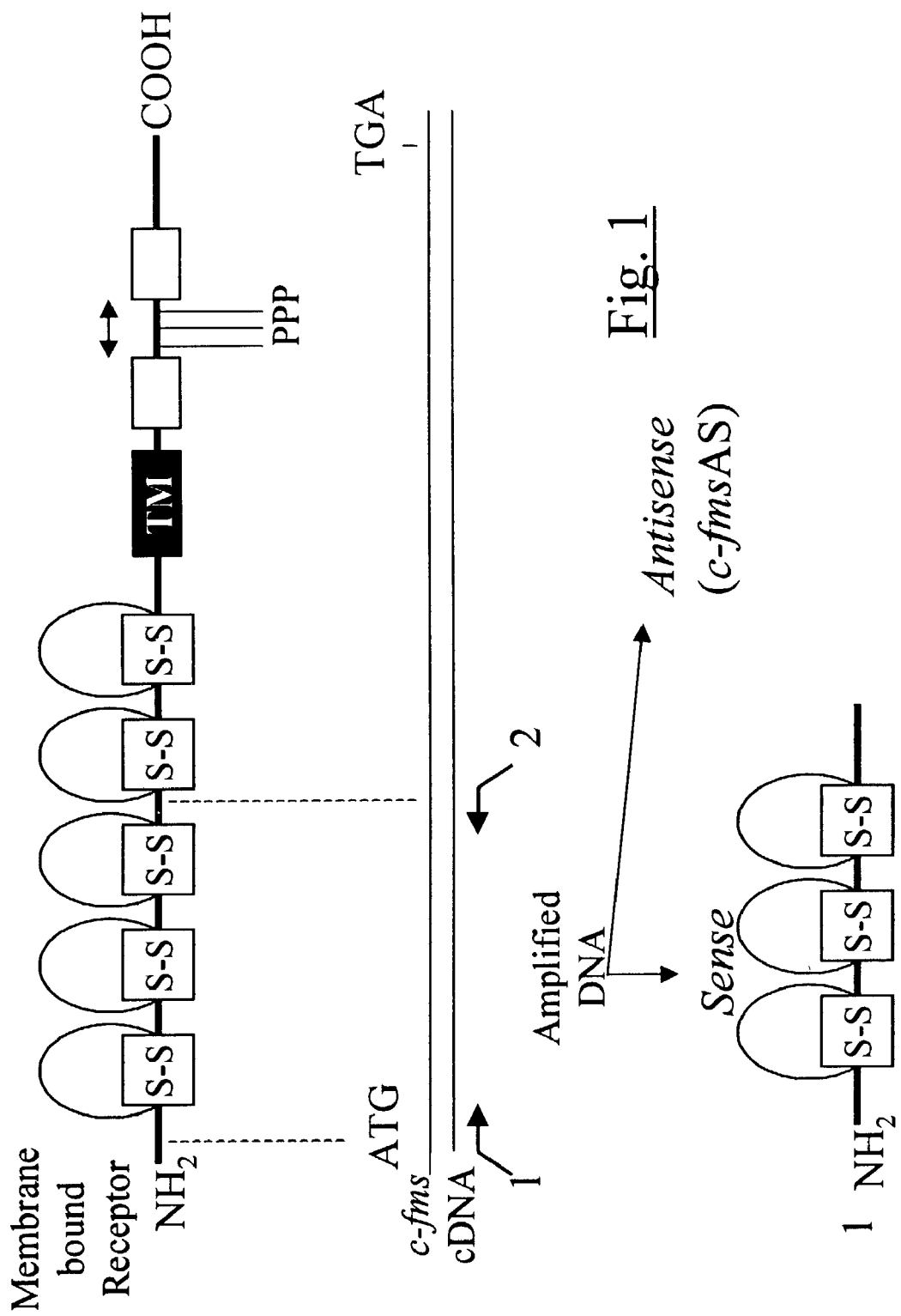
FIG. 1 illustrates a strategy according to one embodiment of the invention to generate c-fms sequences expressing either antisense RNA or soluble protein according to the present invention. The upper line of the diagram shows the predicted entire protein structure of the murine c-fms receptor including the extracellular, transmembrane (TM) and cytoplasmic domains. The individual immunoglobulin-like subdomains and intrasubdomain disulfide bonds (s—s) are shown. The c-fms cDNA with the ATG start codon and the TGA stop codon is shown. The region marked with dotted lines indicates the region that encodes the ligand (M-CSF) binding domain. The cDNA encoding soluble c-fms is amplified using primers 1 and 2 as shown. The amino acid number contained in the soluble segment is shown. Proteolytic cleavage of pro-c-fms would remove the N-terminal 19 amino acids.

Methods of the present invention utilize RNA and protein-based inhibitors to inhibit M-CSF activity by interfering with the production and/or biological activity of a native c-fms receptor. One can use these methods to treat any disease in which inhibiting M-CSF activity has a beneficial effect on a patient (ameliorating a disease, lessening the severity of its complications, preventing it from recurring, or merely preventing it from worsening are examples of beneficial effects). Many diseases are known in the art in which M-CSF activity is known or suspected to play a role in initiating, aggravating, or maintaining the pathological state that comprises the disease. Atherosclerosis, osteoporosis, arthritis, Alzheimer's, nephritis (glomerular, IgA, and lupus), and diabetes mellitus (type 1 and/or type 2), infectious diseases, cancer, inflammatory diseases and inherited disorders characterized by defects in one or more components in the M-CSF signaling pathway.

Embodiments of the present invention are directed primarily, but not exclusively, to a method for treating and preventing cardiovascular disease by inhibiting receptors to M-CSF. Other embodiments of the present invention include any and all biologic and/or pathobiologic phenomena mediated in whole or in part by M-CSF signaling through its receptor. Pathobiologic phenomena include, but are not limited to, disease entities such as osteoporosis, Alzheimer's disease, diabetes mellitus (Type 1 and/or Type 2), infectious diseases, cancer, and inherited disorders characterized by defects in one or more components in the M-CSF signaling pathway. Methods of the present invention may also be used to treat those diseases in which c-fms is abnormally expressed and/or abnormally functions.

In a preferred embodiment, methods of the invention are used to inhibit atherosclerosis, and to thereby treat the cardiovascular diseases that atherosclerosis causes. These methods may be used in any patient who could benefit from reducing atherosclerosis that is already present, from inhibiting atherosclerosis that has yet to form, or from both reducing existing atherosclerosis and inhibiting new atherosclerosis. Such patients include those suffering from, for example, angina pectoris and its subtypes (e.g., unstable angina and variant angina); ischemias affecting organs such as the brain, heart, bone, and intestines, and conditions associated with these ischemias, such as stroke, transient ischemic attacks, heart attack, osteonecrosis, colitis, poor kidney function, and congestive heart failure; poor blood circulation to the extremities and the complications of poor blood circulation, such as slow wound healing, infections, and claudication; atherosclerosis itself, including restenosis following angioplasty of atherosclerotic lesions; and other diseases caused by or associated with atherosclerosis.

M-CSF/c-fms dependent cell signaling can be disrupted in several ways according to methods of the invention: one can, for example, follow a nucleic-acid based approach that inhibits or suppresses the expression of c-fms RNA; or one can follow a protein-based approach to interfere with the biological activity of the membrane bound c-fms.

A monoclonal antibody against the ligand binding domains of the M-CSF receptor (c-fms) was initially utilized by the inventor to inhibit the biological effects of M-CSF in LDLR-deficient mice. Macrophages isolated from LDLR-deficient and control C57BL/6 mice showed positive immunoreactivity to the c-fms monoclonal antibody. Both control and LDLR-deficient mice on a C57BL/6 genetic background of 7 to 10 weeks of age, when injected intraperitonealy with 0.5 mg/day of the c-fms antibody every alternate day, exhibited increased levels of serum cholesterol and decreased numbers of monocytes in circulation as compared to mice injected with either saline or an isotyped antibody control. There were features of osteopterosis noted as well, including mild growth retardation in mice injected with the anti-c-fms monoclonal antibody. When LDLR-deficient mice were fed a pro-atherogenic diet, mean aortic atherosclerotic lesion area was significantly reduced by injecting c-fms antibody compared to their uninjected littermates on the same diet. Analysis of variance between antibody injected vs. uninjected LDLR-deficient mice (n=6) revealed that this difference was significant ($p<0.01$). The atheromatous lesions in the c-fms antibody injected LDLR-deficient mice showed highly reduced numbers of monocyte-macrophages as examined by immunohistochemistry. Although the monoclonal antibody based method exhibited effectiveness in reducing atherosclerosis, it was labor-intensive and expensive. It moreover required frequent intravenous injections of c-fms monoclonal antibody, which could limit the practical and widespread applicability of this approach in humans. Alternative means of delivering effective doses of therapeutic c-fms inhibitors were therefore desirable.

One aspect of the present invention evaluates the feasibility and efficacy of somatic cell gene transfer utilizing viral vectors containing c-fms gene sequences that express antisense RNA. Appropriate viral vectors that can express antisense c-fms RNA include expression vectors based on recombinant adenovirus, adeno-associated virus, retroviruses or lentivurses. An ideal vector for c-fms antisense gene transfer against atherosclerosis and angioplasty/stent-induced restenosis in mammals has the following attributes: (1) high efficiency of in vivo gene transfer; (2) recombinant gene expression in dividing as well as nondividing cells (the baseline mitotic rate in the coronary artery wall is <1% even in advanced lesions); (3) rapid and long-lived recombinant gene expression; (4) minimal vascular toxicity from inflammatory or immune responses; (5) absence of baseline immunity to the vector in the majority of the population; and (6) lack of pathogenicity of viral vectors. This is not to say that a vector must have all of these attributes; indeed, many useful vectors will not.

In a preferred embodiment of the invention, one employs adenovirus serotype 5 (Ad5)-based vectors (Quantum Biotechnology, Inc., Montreal, Quebec, Canada) to deliver and express c-fms gene sequences expressing antisense RNA in cultured macrophages and vascular smooth muscle cells and in atherosclerosis-prone mice and swine. The recombinant Ad5 vectors have several advantages over other vectors such as liposomes and retroviruses. Unlike retroviral vectors, proliferation of the target cell is not required for infection by adenovirus vectors and thus, Ad5 vectors can infect cells in vivo in their quiescent state. Ad5 vectors are capable of infecting a number of different tissues although the transduction efficiency can vary according to the cell type. Ad5 vectors as a means of in vivo gene delivery have certain drawbacks: (1) gene expression from cells transduced with the Ad5 vector is often transient due to the elimination of the Ad5-transduced cells by the host immune system; (2) Ad5 vectors may generate some toxicity to human recipients as observed in human clinical trials in cystic fibrosis patients; and (3) initial administration of Ad5 vectors produces blocking antibodies to the vectors, thereby decreasing the effectiveness of repeated administrations. Ad5 vectors are preferred nonetheless, and may be used to effectively practice the methods of the invention described herein.

Using reverse transcripatse polymerase chain reaction (RT-PCR), a portion of c-fms mRNA corresponding to 976 nucleotides from the 5'-terminus is isolated and cloned upstream to the human cytomegalovirus (CMV) major immediate early promoter-enhancer in a direction to generate antisense c-fms RNA. The use of recombinant Ad5 vectors demonstrates the usefulness of gene transfer for the delivery of therapeutic antisense RNA in murine and swine models, and shows that adenovirus-mediated gene therapy can be particularly well suited as an adjunct to coronary angioplasty, since even temporary inhibition of smooth muscle cell proliferation could suffice to limit the formation of restenotic lesions.

A second embodiment of the present invention provides a method of gene therapy to produce high levels of soluble forms of membrane bound c-fms protein that competes for non-bound M-CSF but lacks all of its signal transduction domain. The three N-terminal immunoglobulin-like domains of the c-fms receptor protein constitute the high-affinity M-CSF binding region (the fourth and fifth immunoglobulin-like domains perform functions other than ligand binding). Z. Wang et al, "Identification of the ligand-binding regions in the macrophage colony-stimulating factor receptor extracellular domain," *Mol Cell Biol*, 13:5348–5359 (1993). The method involves cloning of a portion of c-fms mRNA corresponding to the three N-terminal immunoglobulin-like domains using a combination of an upstream and a downstream primer. A 976-nucleotides long amplified cDNA is cloned upstream to the CMV promoter/enhancer in an adenoviral expression plasmid. Using the calcium phosphate transfection method, 293T cell cultures is transfected with 5 mg of soluble c-fms/rAd5 plasmid DNA followed by a 48-hour period to allow for expression and secretion of c-fms into the cell media. The medium from cells transfected with the soluble c-fms/rAd plasmid contains a secreted c-fms protein concentration up to 33 ng/ml. To increase this relatively low soluble c-fms expression, newer versions of rAd vectors that employ different promoters including the human U1 promoter, native human c-fms gene promoter or tetracycline-inducible promoter can be employed. In vitro assays shows that the soluble c-fms binds M-CSF with high-affinity and inhibits the growth and survival of mouse bone marrow derived macrophages.

As with many other type of diseases, therapeutic strategies to treat atherosclerotic disease entail treatment for an extended period of time ranging from months to years.

Prolonged and efficient transgene transcription from heterologous promoters is a major consideration for gene therapies. The CMV promoter to drive expression of soluble c-fms in the present invention has been popularly used to express a variety of genes; it is, however, often subject to epigenetic silencing as are most promoters and transgenes. In an attempt to circumvent this problem, a variety of promoter expression strategies can be used to optimize the in vivo production of the soluble c-fms in the present invention. Efficient gene expression in viral vectors depends upon a variety of factors. These include promoter strength, message stability and translational efficiency. Each of these factors must be explored independently to achieve optimal expression of soluble c-fms gene. Applications of other promoter/enhancer variants to increase and optimize the expression of soluble c-fms in vitro as well as in vivo are included within the scope of this invention. These include promoters or enhancers that are stronger than CMV or that exhibit inducibilty. Tetracycline-inducible promoters, for example, or promoters that are tissue-specific, such as vascular-endothelial or smooth-muscle specific promoters/enhancers, may be used to produce sufficient amounts of soluble c-fms or its derivative. The presence of soluble c-fms or its derivative reduces the amount of M-CSF ligand available for binding and thereby inhibits the M-CSF/c-fms cell signaling pathway. Levels and persistence of soluble c-fms expression can be compared with those obtained from the CMV promoter.

A third embodiment of the invention administers a ribozyme-viral (adeno, adeno-associated or lentiviral) vector against c-fms mRNA in a mammal. The method involves development of a hammerhead ribozyme expression cassette in a viral backbone that targets the GUC sequence in codon 18 of c-fms mRNA. Ribozymes are sequence-specific endoribonucleases that catalytically cleave specific RNA sequences, resulting in irreversible inactivation of the target mRNA, thereby inhibiting the gene expression. T. Cech. "Biological catalysis by RNA," *Ann Rev Biochem,* 55:599–629 (1986); J. J. Rossi, "Therapeutic ribozymes: principles and applications," *Bio Drugs,* 9:1–10 (1998). Ribozymes display catalytic activity that lowers the amount required for inhibiting gene expression, and in this way offer an advantage over antisense ODN. Ribozymes can be delivered exogenously or can be expressed endogenously with the use of appropriate promoters in a viral vector. In a preferred embodiment of the invention, one uses a hammerhead ribozyme directed to human c-fms mRNA; this ribozyme restricts the growth of peripheral blood derived macrophages in vitro. Cationic liposome-mediated transfection of macrophages with ribozymes against c-fms causes reduced cell growth and survival as determined by MTT assay. Fluorescent modified ribozymes are used to determine the efficiency of cellular uptake and optimal delivery conditions in cultured human macrophages. The results of the in vitro studies provide the basis for the in vivo usage of ribozymes to inhibit the growth and survival of macrophages in atherosclerotic lesions. Desired quantity or the length of expression of the ribozyme-viral vector can be readily determined without undue experimentation, as can the most effective and/or convenient route of administration.

In a fourth embodiment of the invention, there is provided a non-viral method to inhibit the expression of c-fms receptor. This method involves synthesis of pentadecamer (15-mer) ODN corresponding to the sense and antisense sequense of the human c-fms mRNA. Pentadecamer ODN are known to bind very strongly to single-stranded regions of the target mRNA (D Jaskuski et al., "Inhibition of cellular proliferation by antisense oligonucleotide to PCNA cyclin," *Science,* 240:1544–1548, (1988)) and thereby to strongly inhibit translation of the mRNA. In a preferred embodiment, four ODN are synthesized on an automated solid-phases synthesizer (Applied Biosystem, Inc., Rockville, Md.) and purified using standard protocols. Two of the ODN are complementary to first 15 nucleotides of either the sense (SEQ ID NO. 1) or antisense (SEQ ID NO. 2) strand of human c-fms mRNA starting with the initiation codon (AUG). The other two ODN are 50% or less base-pair mismatch (SEQ ID NO. 3, SEQ ID NO. 4) with the antisense mRNA. Inhibition of cell proliferation of peripheral blood derived macrophages by antisense c-fms ODN is dose-dependent over the range of 2 to 15 micromolar (μM) over a 24 hour period. A single 7 μM dose of antisense c-fms ODN inhibited cell proliferation by 57 to 75% whereas the same concentration of sense ODN inhibited proliferation by only 19%. Control ODN did not show any detectable effects on macrophage cell proliferation. The method shows that growth of cultured macrophages is inhibited by the interaction of antisense c-fms ODN with the endogenous c-fms mRNA and provides evidence in favor of the using antsense c-fms ODN to inhibit the expression of c-fms in vivo, thereby blocking the M-CSF/c-fms mediated cell signaling in a mammal.

The vascular delivery of viral vectors expressing antisense c-fms RNA, soluble c-fms protein or ribozyme and non-viral antisense ODN in the present invention can be accomplished using a wide range of local delivery devices and methods. K. L. March, "Methods of local gene delivery to vascular tissues," *Semin Intervent Cardiol,* 1:215–223 (1996). The rationale behind local delivery is that site-specific delivery of vectors may result in maximal therapeutic efficacy with minimal systemic side effects. These local delivery devices typically entail an endovascular or "inside-out" approach whereby therapeutic agents are delivered to the target site via intravascular catheters or devices. Although gene transfer is demonstrated for each device, most studies of catheter-based gene transfer reveal low efficiency, rapid redistribution of the infused material, and escape of the infusate into the systemic circulation. Recently, several devices with modified needles capable of direct injection into interstitial tissue of either myocardium or vasculature are described. One such approach to local drug delivery is via the nipple balloon catheter, or INFILTRATOR® (InterVentional Technologies, Inc., San Diego, Calif.). Use of the INFILTRATOR® for intramural delivery of small volumes of high-titer rAd5 is preferred. The INFILTRATOR® catheter offers improved local gene delivery by placing vector particles directly deep within the vascular wall. The INFILTRATOR® catheter is designed to provide direct intramural delivery of agents by mechanical access into the media and inner adventitia, which is achieved using sharp edged injection orifices mounted on the balloon surface. P. Barath et al. "Nipple balloon catheter," *Semin Intervent Cardiol,* 1:43 (1996). This catheter has been used clinically, G. S. Pavlides et al, "Intramural drug delivery by direct injection within the arterial wall: first clinical experience with a novel intracoronary delivery-infiltrator system," *Cathet Cardiovasc Diagn,* 41:287–292 (1997), and has been demonstrated to yield enhanced local transduction efficiency by adenoviral vectors compared with that achievable by endoluminal delivery. T. Asahara et al., "Local delivery of vascular endothelial growth factor accelerates reendothelialization and attenuates intimal hyperplasia in balloon-injured rat carotid artery," *Circulation,* 91:2793–2801 (1995).

In an alternate embodiment, one can utilize perivascular or "outside-in" drug delivery in the vessel wall by modifying the procedure of periadventitial carotid injury in the mouse. Oguchi S, et al. "Increased intimal thickening after arterial injury in hypercholesterolemic apolipoprotein E-deficient mice: finding a novel method," *Circulation* Supplement I-548,3066, (1997); Dimayuga P, et al. "Reconstituted HDL containing human apolipoprotein A-1 reduces VCAM-1 expression and neointima formation following periadventitial cuff-induced carotid injury in apo E null mice" *Biochem Biophys Res Commun,* 264:465–468, (1999). Apo E-deficient mice (20-weeks of age, 6 per group) are anesthetized, and the carotid artery is exposed by making a small incision in the side of the neck. In one of the inventor's experiments, a section of artery was loosely sheathed with a cuff made of a Tygon tube (3.0-mm long, 0.50-mm inner diameter). A biodegradable biocompatible polymeric material, ATRI-GEL®, (Atrix Laboratories, Ft. Collins, Colo.), a copolymer of polylactic and polyglycolic acid, was used for the local delivery of viral particles. 18% (w/w) polymeric gel in PBS with $1\times10^8$ pfu of rAd5 (right) or without rAd5 (left carotid) was applied between the cuff and the vessel using a syringe and blunt cannula. The gel compound used in the study exists as a free-flowing liquid below body temperature. When placed in an aqueous environment at or above body temperature, the viscosity increases and the gel solidifies into a viscous mass. Once applied to the artery in vivo, the polymer gels immediately on contact and the gel is then gradually resorbed in about 14 to 21 days, thereby providing potential use as a drug depot. The gel releases viral particles that cause a reversal in the effects of periadventitial injury on neointimal response to carotid injury in apo E-deficient mice.

The introduction of surgical and percutaneous arterial revascularization to treat atherosclerosis has profoundly altered the clinical management of disease, but has also brought unanticipated problems and unanswered questions. In particular, surgical and especially percutaneous revascularization may elicit an exaggerated healing response, which in many respects is similar to the development of de novo atherosclerotic lesions. This "response to injury" is more proliferative in nature than de novo lesion formation, but may nevertheless lead to restenosis, or even late or abrupt vessel closure, and ultimately result in a failed revascularization attempt. For this and other additional reasons, long-term clinical studies have documented improved outcomes only in selected patient subgroups; for those with stable angina pectoris, coronary intervention remains merely palliative, and does not alter the progression or outcome of the underlying causative disease process.

With balloon coronary angioplasty, restenosis rates of 30%–40% or more have been documented, and certain lesion sites and patient subgroups have been found to be particularly susceptible to restenosis. Intensive research efforts into the cause of restenosis have yielded considerable insight, but as yet no unequivocal treatment to eliminate the problem. Technical innovations in revascularization equipment and techniques have shown some success, but even this has been of limited effectiveness. In particular, the development of the intracoronary stent markedly reduced the incidence of restenosis. With proper stent placement techniques, restenosis rates have been reduced to roughly 10%, and so consequently intracoronary stent placement has largely supplanted balloon angioplasty alone as the interventional coronary treatment of choice. Still, given the rapid proliferation and acceptance of intracoronary stenting, even a 10% restenosis rate results in a very large number of patients in whom the revascularization attempt has been unsuccessful, and for whom other treatment strategies have not been convincingly effective. The same patient frequently needs multiple separate interventions, and ultimately these may not be successful.

Since the arterial response to injury is predominantly mitogenic and neoproliferative in nature, intracoronary irradiation (or intracoronary brachytherapy) has been developed and deployed to attempt to reduce further the numbers of patients who restenose following coronary intervention. Intracoronary brachytherapy has also met with limited success, however; and unfortunately has brought with it two new manifestations of the disease as a side effect: geometric miss and late in-stent thrombosis. It appears likely that these two effects will significantly limit the efficacy of intracoronary brachytherapy as a definitive treatment for restenosis. Thus, a need remains for an effective way to limit or eliminate restenosis following coronary stent placement. Alternatively, if intracoronary brachytherapy is to achieve unequivocal effectiveness in eliminating restenosis following stent placement, a solution to late in-stent thrombosis and geometric miss must be found.

One attractive approach to treating restenosis following stent implantation is by modifying the stent to directly influence the cytokines involved in the response to injury that implanting the stent causes. M-CSF expression is rapidly increased following arterial injury, and abnormally elevated expression levels persist for several weeks thereafter. However, in mice with a targeted deletion of the gene encoding M-CSF, this increased expression of M-CSF cannot occur, and consequently neointimal proliferation following arterial injury is sharply reduced or even abolished entirely. Thus, inhibition of M-CSF signaling provides an attractive gene therapeutic treatment strategy.

In one embodiment of the invention, one coats a stent with rAd5 expressing c-fms inhibitors (e.g. antisense RNA, soluble c-fms protein, ribozyme) or a compound containing ODN to inhibit and diminish M-CSF/c-fms cell signaling. Any stent known in the art may be used for this purpose; this permits one to employ the method of the invention without increasing the time required to implant the stent, and also will not require significant additional equipment, expertise, hospitalization, or expense. This procedure diminishes the need for repeat hospitalizations and additional interventional procedures. It also ameliorates geometric miss and late in-stent thrombosis following intracoronary brachytherapy.

EXAMPLES

The following examples are typical of the procedures that may be used to inhibit M-CSF by disrupting the M-CSF/c-fms cell-signaling pathway. Modifications of these examples will be apparent to those skilled in or familiar with such procedures.

The use of carefully defined animal models is essential to investigate pathophysiologic mechanisms and to assess therapeutic strategies aimed at modifying the arterial luminal narrowing that often occurs following atherosclerosis or vascular injury (restenosis) in humans. The inventor used both large and small animals to establish the effects of c-fms inhibitors on the development and progression of atherosclerotic and restenotic lesions. Atherosclerosis prone apo E and LDLR-deficient mice are extremely useful in this regard as they exhibit very similar atherosclerotic lesions as known in humans. One can extend studies using a mouse model of atheroscelrosis and arterial injury to a large animal model to examine the effects of local gene delivery on the coronary arterial luminal narrowing following balloon overstretch and stent overinflation injury in swine. Swine model for coronary injury offers advantages over other animal models because it resembles to human disease. These advantages include: (1) identical cardiac and coronary size and anatomy; hence, coronary injury can be induced with clinical angioplasty balloon catheters and stents; (2) similar platelet-coagulation systems; (3) similar mechanics of vascular injury as encountered in clinical angioplasty and stenting, e.g., medial dilatation and/or dissection; (4) balanced contribution of the thrombotic and the proliferative processes to neointimal formation; and (5) similarities in topographic and histologic characteristics of intimal lesions (e.g., non-concentric lesion morphology) Additional similarities of the swine coronary balloon overstretch injury preparation to clinical angioplasty in humans include similar mechanisms of luminal narrowing following the procedure, including elastic recoil (acute remodeling), vasoconstriction, inadequate compensatory enlargement (chronic constrictive remodeling), SMC proliferation and extracellular matrix synthesis. H. Luo et al., "Coronary artery restenosis after balloon angioplasty in humans is associated with circumferential coronary constriction," *Arterioscler Thromb Vasc Biol*, 16:1393–1398 (1996); H. R. Andersen, "Remodeling rather than neointimal formation explains luminal narrowing after deep vessel wall injury," *Circulation*, 93:1716–1724 (1996).

Example 1

Cloning of c-fms Gene Sequences Expressing Antisense RNA or Soluble Protein

RT-PCR was performed to amplify c-fms gene DNA sequences corresponding to the ligand binding domain of the receptor using specific sets of primers on the DNA template produced from mouse or human macrophage mRNA. Human macrophages were grown from peripheral blood monocytes following standard protocols. Mouse macrophages were derived from bone marrow cells. Total cellular RNA was isolated by lysis of mouse or human macrophages in guanidinium isothiocyanate, phenol-chloroform extraction and ethanol precipitation. P Chomzynski, N Sacchi. "Single-step method of RNA isolation by acid guanidinium thiocyanate-phenol-chloroform extraction. *Anal Biochem*. 162:156–159 (1987). To amplify the mouse and human c-fms gene sequence corresponding to the ligand binding domain (FIG. 1) two primers (cfms-1, SEQ ID NO. 5, nucleotides 75 to 93; and cfms-2, SEQ ID NO. 6, nucleotides 994 to 1008) were synthesized corresponding to the high affinity M-CSF binding region. Z. Wang et al., "Identification of the ligand-binding regions in the macrophage colony-stimulating factor receptor extracellular domain," *Mol Cell Biol*, 13:5348–5359 (1993). RT-PCR was performed to amplify a 976 nucleotides long cDNA sequence using total RNA prepared from human or mouse macrophages as substrate. The amplified products were subcloned in pCRII vector (Invitrogen, San Diego, Calif.). Diagnostic restriction digestion and DNA sequencing were performed to establish the identity of the mouse or human c-fms gene sequences.

Example 2

Construction and Purification of Recombinant Adenoviral Viral Vectors Expressing Either Antisense RNA or Soluble Protein The choice of the Ad5 gene delivery system for c-fms gene was based on its ease of use, and many attractive features that allow the efficient transfer of genetic material as compared to other viral and non-viral (e.g., "naked" DNA or lipid coated DNA) gene delivery systems. Ad5 produces stable virions with high titers that are capable of transducing replicative and non-replicative cells. Ad5 has a wide host and tissue range and exhibits low pathogenicity in humans.

Figure 2:
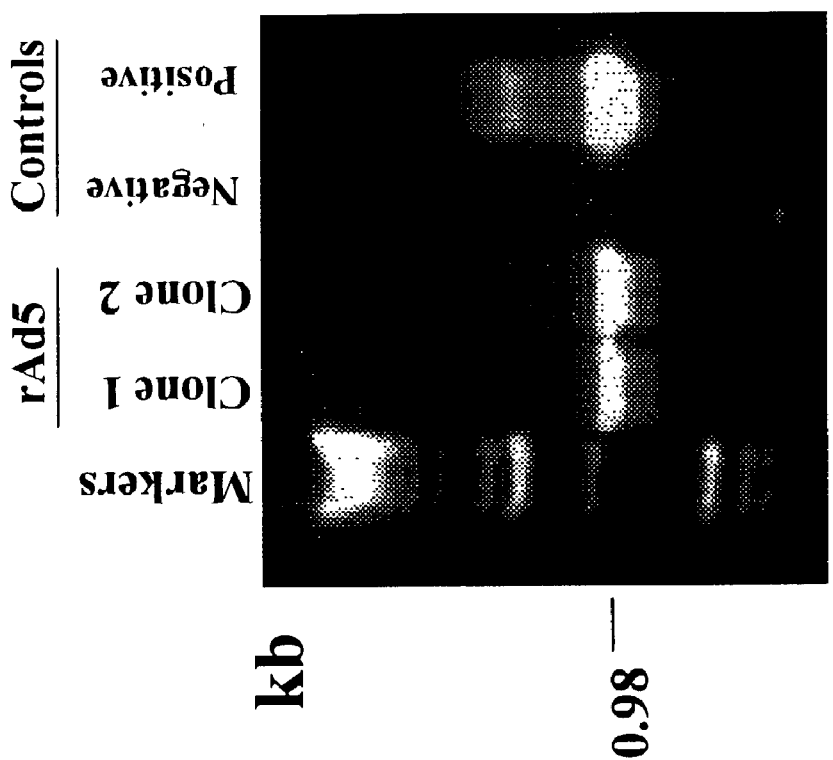
FIG. 2 illustrates a map of an adenoviral (Ad5) transfer vector used in a preferred embodiment of the invention and the PCR genotyping for the recombinant Ad5 expressing sense and antisense c-fms sequences.
Figure 2:
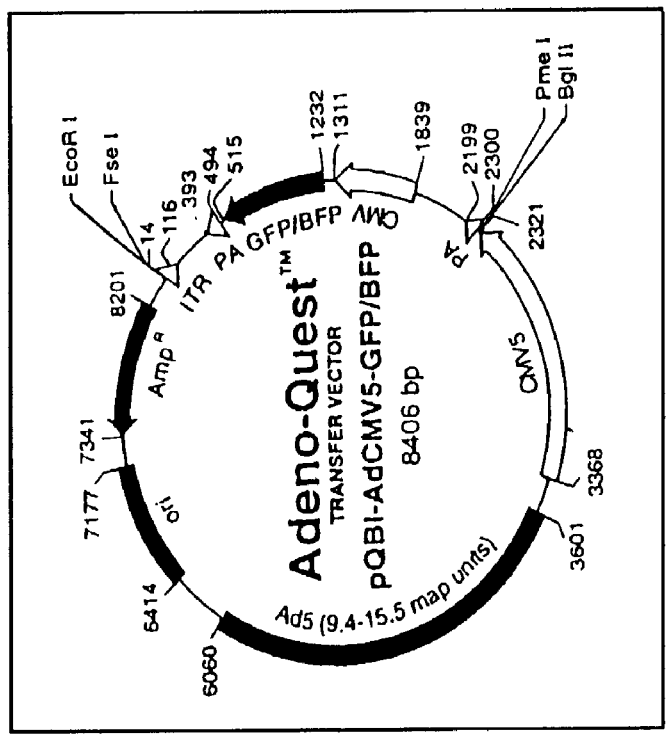

A 976 base pair EcoRI fragment of mouse c-fms cDNA was excised from pCRII plasmid and gel purified. For recombinant adenoviral transfer vector construction, BgIII linkers were attached to the 976 base pair fragment comprising the protein coding region of c-fms gene. This fragment was then ligated to a BgIII linearized transfer vector pQBIAdCMV5-GFP (Quantum Biotechnology, Inc., Montreal, Quebec, Canada) between the strong enhance/promoter of the CMV immediate early genes and the SV40 polyadenylation signal (FIG. 2). The presence of 976-base pair fragment in the transfer vector clones was confirmed by performing PCR using mcfms-1 and mcfms-2 primers. The orientation of the c-fms fragment with regard to the CMV promoter enhancer was determined by double restriction digestion of the recombinant adenoviral transfer vectors using BglII and ApaI restriction enzymes. ApaI was a convenient asymmetrical site in the c-fms cDNA insert. DNA sequencing was carried out on the clones of the transfer vector that contained mouse c-fms fragment. Recombinant transfer vector containing both right and wrong orientation of c-fms fragment were individually isolated and purified.

To produce the recombinant viral particle, recombinant adenoviral transfer plasmid was linearized with EcoRI. The linearized DNA was extracted once with buffer-saturated phenol and choloroform/isoamyl alcohol (24:1), precipitated with 1/10 volume of 3M NaAcetate pH 5.2 and 2.5 volumes of ethanol and resuspended in Tris-EDTA buffer. The concentration of the linearized plasmid was estimated on an agarose gel. 5 µg of linearized transfer plasmids containing the c-fms gene were mixed with 5 µg of adenoviral DNA and transfected onto sub-confluent 293 A cells in a 60 mm petridish using the standard calcium phosphate technique. 293A cells line is a permanent line of primary human embryonic kidney cells transformed by sheared Ad5 DNA. This cell lines contains the E1A and E1B, Ad5 genes that complement these genes deleted in the recombinant adenovirus. After overnight incubation, the co-precipitated DNA-calcium phosphate was removed and cells were washed with phosphate-buffered saline (PBS). The cells were split into 6 well plate and left to attach for 6 hours followed by overlayering with agarose following the protocol described in the Adeno-Quest kit supplied by Quantum Biotechnology.

Recombinant Ad5 plaques were screened for the expression of the c-fms gene sequences and viral stocks of the first amplification were prepared. Each clone was tested for the expression of recombinant protein and/or virus production. A final round of PCR was performed to fully characterize the rAd5 that express either antisense c-fms RNA or soluble c-fms protein. Large scale production of high titer viral recombinant particles were carried out in 293 A cells. This involved a sequential increase in cell culture size and adenovirus infection cycles. Purification of recombinant Ad5 expressing either antisense c-fms (Ad5CMVc-fmsAS) or soluble protein (Ad5CMVc-fmsSA) was accomplished by double cesium chloride gradient. Titration of the recombinant viral particle were carried out using a combination of plaque assay method and real time PCR (Applied Biosystems, Calif.)

Example 3

Figure 3:
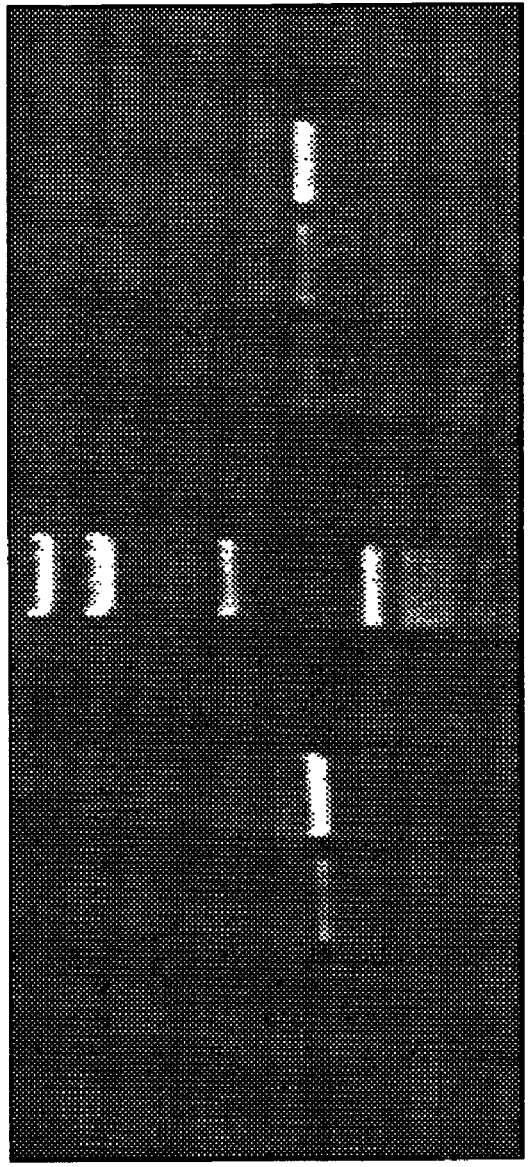
FIG. 3 shows a RT-PCR assay for c-fms antisense RNA.
Figure 4:
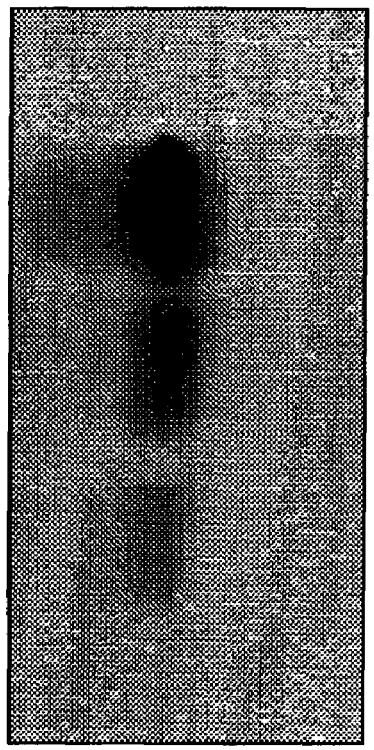
FIG. 4 shows a Northern blot analysis of c-fms antisense RNA.

Adenovirus Mediated c-fms Gene Transduction in Cultured Human and Mouse Macrophages Macrophages, derived from either from human peripheral blood monocytes or from mouse bone marrow, were transduced with adenoviral vectors expressing antisense c-fms RNA (Ad5CMVc-fmsAS) or soluble c-fms protein (Ad5CMVc-fmsSA) linked to green fluorescence protein (GFP) to allow sorting of positive transfectants. Transfection efficiency of the recombinant virus at different MOI was determined by direct visualization and flow cytometric analysis of GFP fluorescent activity. The repression of c-fms in Ad5CMVc-fmsAS transduced macrophages was assessed 2 to 3 days post transduction by flow cytometry using human or murine c-fms specific antibodies. Antisense c-fms RNA effectively inhibited the expression of c-fms protein as shown by immunoblot analysis in a dose and time dependent manner. Cultured macrophages showed reduced growth in response to both antisense c-fms RNA expression and with the expression of soluble protein as early as 1 day post transduction. As shown in FIG. 3, by 2 days (48 hours) post transduction with Ad5CMVc-fmsAS there were abundant detachment of macrophages from tissue culture dish. These cell showed rounding off with continued expression of GFP. MTT cell survival assay was used to measure changes in cell survival at various time point post transduction. Results of this experiment show that macrophages were successfully transduced with adenoviral vectors expressing antisense c-fms RNA (FIG. 3) or soluble c-fms. Expression of these molecules by macrophages was associated with poor growth and reduced survival (FIG. 4A and B). Collectively, these results suggest a potent inhibitory effect of the adenoviral expressed antisense c-fms RNA and soluble c-fms suggesting that both strategy could be exploited to inhibit the survival and activation of mononuclear phagocytic cells and atherogenesis.

Example 4

Studies with Cultured Mouse, Pig and Human Vascular Smooth Muscle Cells

Figure 5:
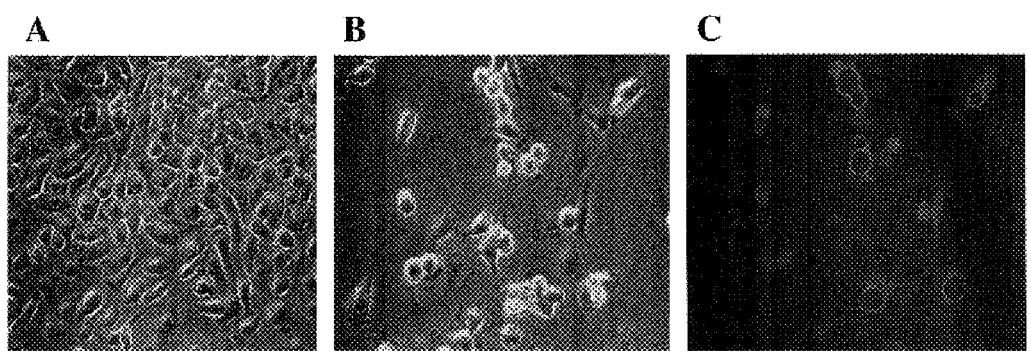
FIGS. 5A–5C (color) show that infection of cultured macrophages with Ad5CMVc-fmsAS inhibits the growth of macrophages in a time-dependent manner (A is at 0 hours; B is at 48 hours; C depicts detection of green fluorescence protein (GFP) at 48 hours).
Figure 6A:
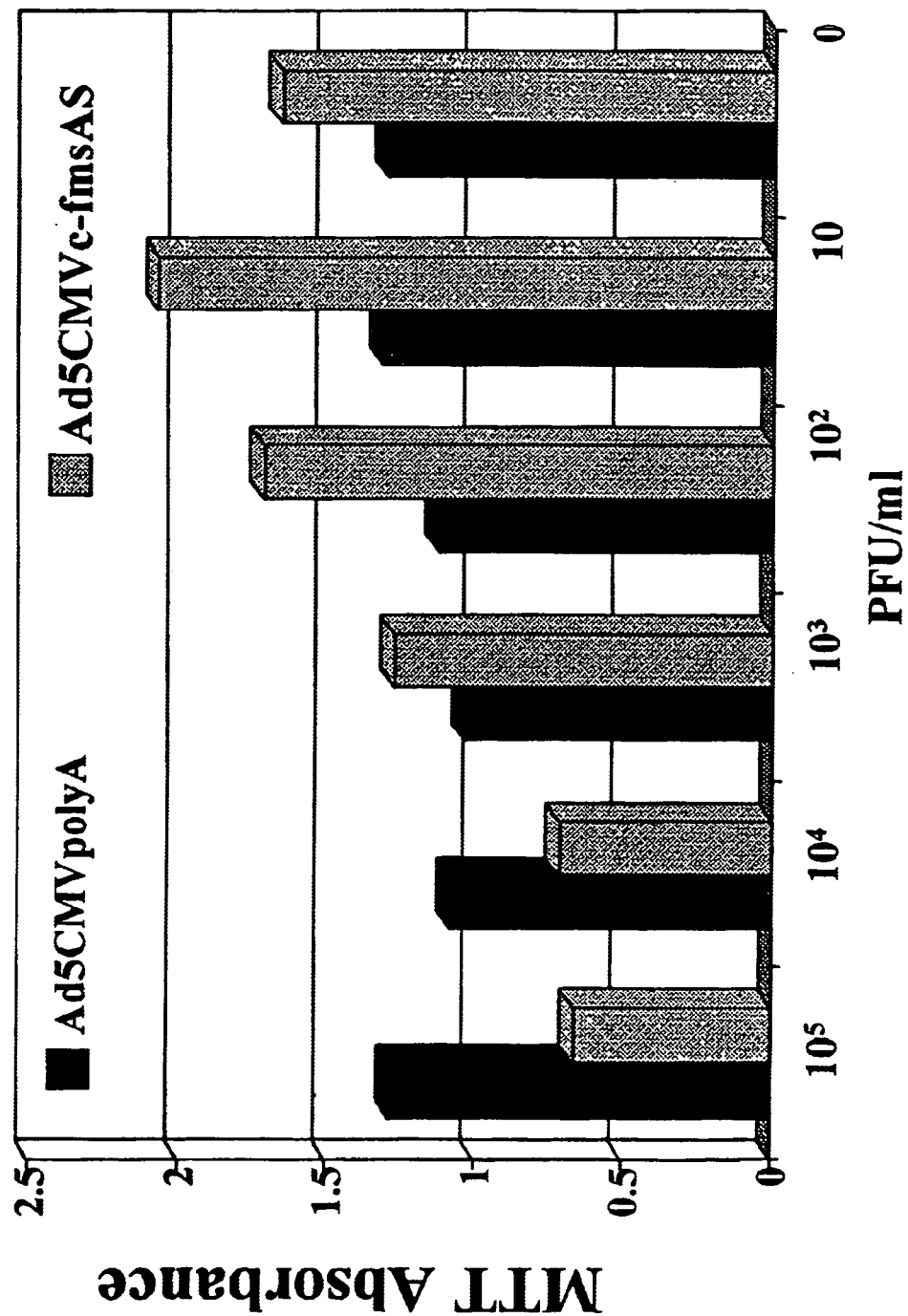
FIGS. 6A and 6B illustrate that infection with Ad5CMVc-fmsAS inhibits cell survival in cultured macrophage (Mϕ) in a dose-dependent manner.
Figure 6B:
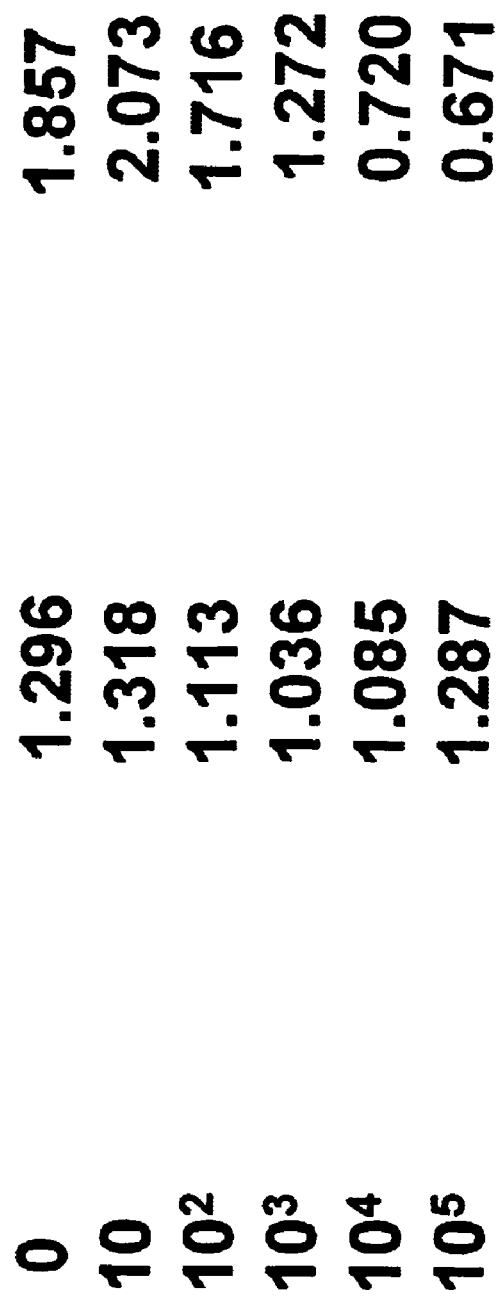
Figure 7:
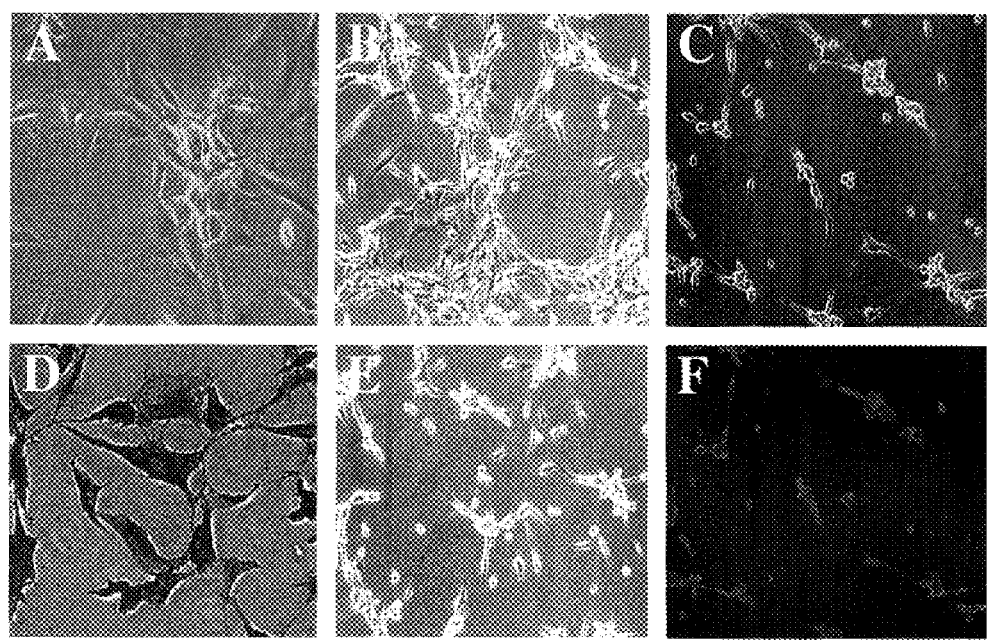
FIGS. 7A–7F (color) show infection of mouse vascular SMC with Ad5CMVc-fmsAS (A and D are at 0 hours, D depicts a staining for α-actin; B and E are at 48 hours; C and F are at 72 hours, F depicts detection of GFP).
Figure 8:
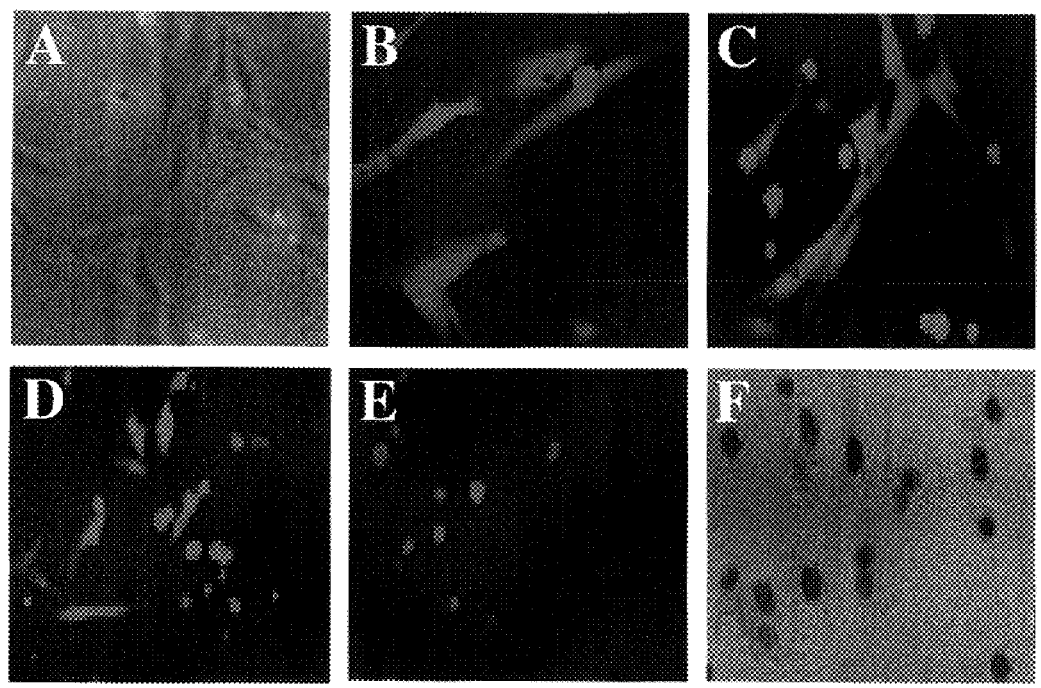
FIGS. 8A–8F (color) show infection of human coronary artery SMC with Ad5CMVc-fmsAS (A is at 0 hours; B, C, D, and E depict detection of GFP at 24 hours, 48 hours, 72 hours, and 96 hours, respectively; F depicts TUNEL staining at 48 hours).

In vitro transducibility of the recombinant viral particles expressing antisense c-fms transgene was assessed by infecting smooth muscle cells derived from mouse, pig and human vessel wall (FIG. 5 to 8). Harvesting of vascular SMC from mouse, pig and human were done using standard procedures. Cell viability was assessed by Trypan blue exclusion. Morphologically typical SMC were observed under the light microscope, and the immunocytochemical staining of a specific SMC marker α-actin was adapted for the identification of mouse vascular SMC (FIG. 5). Mouse, pig and human vascular SMC when transduced with the increasing dose Ad5CMVc-fmsAS showed increased levels of antisense c-fms RNA as determined by RT-PCR (FIG. 6) and Northern blotting assays (FIG. 7). Transduced mouse and human vascular SMC showed high levels of GFP expression while untransduced cells lacked detectable fluorescence. As with macrophages, anisense c-fms RNA inhibited the growth and survival of vascular SMC (FIG. 5 and 8) in a dose and time dependent manner. By 2 days (48 hours) post transduction with Ad5CMVc-fmsAS there were abundant detachment of vascular SMC from tissue culture dish. These cell showed rounding off with continued expression of GFP. Immunostaining for the TUNEL revealed that adenoviral vector dependent expression of antisense c-fms was triggering an accelerated apoptotic process in these cells. Results of this experiment clearly show that vascular SMC can be successfully transduced with adenoviral vectors expressing antisense c-fms RNA. Expression of antisense c-fms RNA by vascular SMC was associated accelerated programmed cell death in these cells. These findings favor a role for M-CSF in the growth and proliferation of vascular SMC suggest that adenoviral expressed antisense c-fms RNA based strategy could be utilized to inhibit the accelerated growth of SMC observed in atherosclerotic and restenotic lesions in humans. The capacity to transduce human coronary SMC opens up the possibility of directly targeting the cells of the arterial wall in inhibiting and/or reversing the development of atherosclerotic or restenotic lesions. The results from this experiment indicate that the encapsidated rAd vectors expressing antisense c-fms RNA are capable of transducing swine VSMC and provide support to study the effects of antisense c-fms gene therapy on injury-induced luminal narrowing in swine.

Example 5

Figure 9:
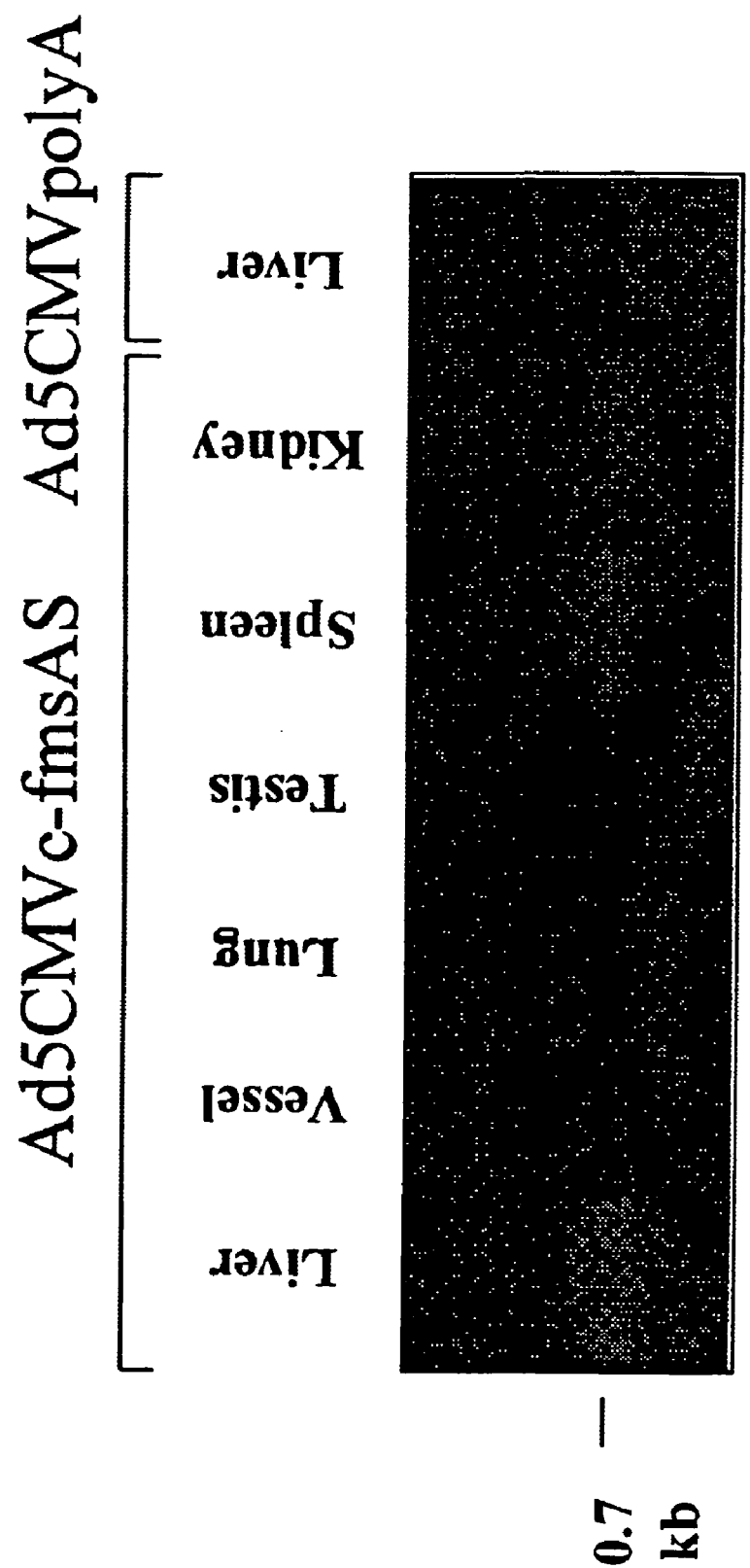
FIG. 9 shows tissue expression of antisense c-fms RNA following in vivo gene transfer of Ad5CMVc-fmsAS particles.

Inhibition of Atherosclerosis by Antisense c-fms RNA and Soluble c-fms Protein Expressed in vivo from Recombinant Ad5 Vectors in the Apo E-deficient Mouse Model The effectiveness of antisense c-fms gene transfer on atherosclerosis was assessed by intravenous IV injection of rAd5 expressing antisense c-fms RNA or soluble c-fms protein in apo E-deficient mice (5 weeks of age) at a $1 \times 10^8$ pfu per animal dose. One group (10 animals per group) of apo E-deficient mice were given the rAd5 vector with the antisense c-fms transgene linked to eGFP reporter and a second group of apo E-deficient mice were administered the rAd5 vector encoding soluble c-fms protein linked to eGFP reporter. Control groups of apo E-deficient mice included (i) untreated mice, (ii) mice receiving a control rAd5 vector with the eGFP gene. Five weeks after the administration of the recombinant virus, one set of animals from all groups were sacrificed and aortas were harvested. In addition, relevant tissue (liver spleen, lung, kidney, testes, and vessel,) were obtained from the dead animals to analyze for the expression of antisense c-fms RNA (FIG. 9), soluble c-fms mRNA, host chromosome integration of the transgenes and host immune response to the rAd5 vectors. For this first set of animals, blood samples were collected at 0, 4, 14, and 35 days after the injections. Ten weeks after administration of the recombinant virus, a second set of mice of all groups were sacrificed and the aforementioned protocol were repeated. For this second set of mice, blood samples will be collected at 0, 4, 14, 35, 56 and 70 days after the injections. Mice were on a cholesterol-rich diet throughout the experiment.

Following anesthesia with enflurane, mice were euthanized and their hearts and aortas were perfusion-fixed with 4% paraformaldehyde, 5% sucrose, 20 mM EDTA at physiologic pH for 10 minutes. The heart and the proximal aorta were then excised and embedded in OCT compound (Tissue-Tek), frozen on dry ice, and then stored at −70° C. until sectioning. Serial 10-μm thick sections, every fifth section from the middle of the ventricle until the appearance of aortic valve and every second section from the appearance to the disappearance of the aortic valve leaflets, were collected on poly-D-lysine-coated slides and stained with Oil Red O and hematoxylin and counter stained with fast green. Quantitation of the Oil Red O stained area in the aortic sinus plaques will be performed by computer-assisted morphometry using IMAGE PRO software and expressed as average of lesion areas from six sections per mouse. The remainder of the thoracic and abdominal aorta (up to bifurcation of common iliac arteries) were removed, stored overnight in formal-sucrose fixative, cut open longitudinally, and stained with Sudan IV to visualize the extent of atherosclerosis of the entire aorta. Quantification of the percentage of aortic surface covered by atheromata were accomplished by computer-assisted planimetry of the Sudan IV-positive areas. In selected sections of the aortic sinus plaques, immunohistochemical staining were performed using monoclonal rat anti-mouse Mac-1 antibody (Boehringer Mannheim Biochemicals) as a marker for mouse monocyte/macrophages and the area of plaque occupied by Mac-1 immunoreactivity were measured using image analysis software described above.

Serum samples were analyzed for total serum cholesterol by enzymatic technique and after precipitation of apo B-containing lipoprotein with phosphotungstic acid, serum HDL cholesterol concentrations were determined. In addition, Northern and Southern blot analyses were performed to determine the tissue expression of the antisense c-fms RNA and the soluble c-fms mRNA and the possible integration of the recombinant viral vector, respectively.

Figure 10:
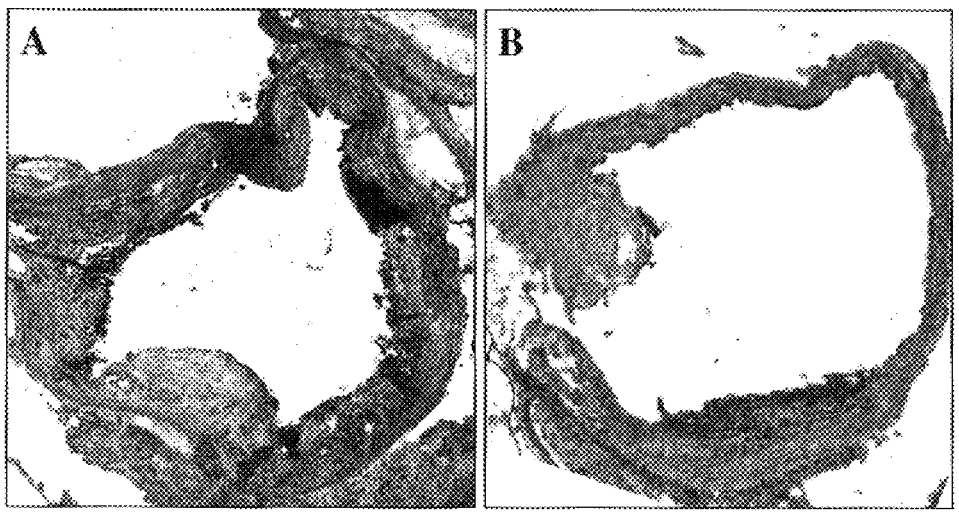
FIGS. 10A and 10B (color) show the effects of c-fms antisense RNA on atherosclerosis in apo E-deficient mice (A depicts a Ad5CMVpolyA treated mouse; B depicts an Ad5CMVc-fmsAS treated mouse).
Figure 11:
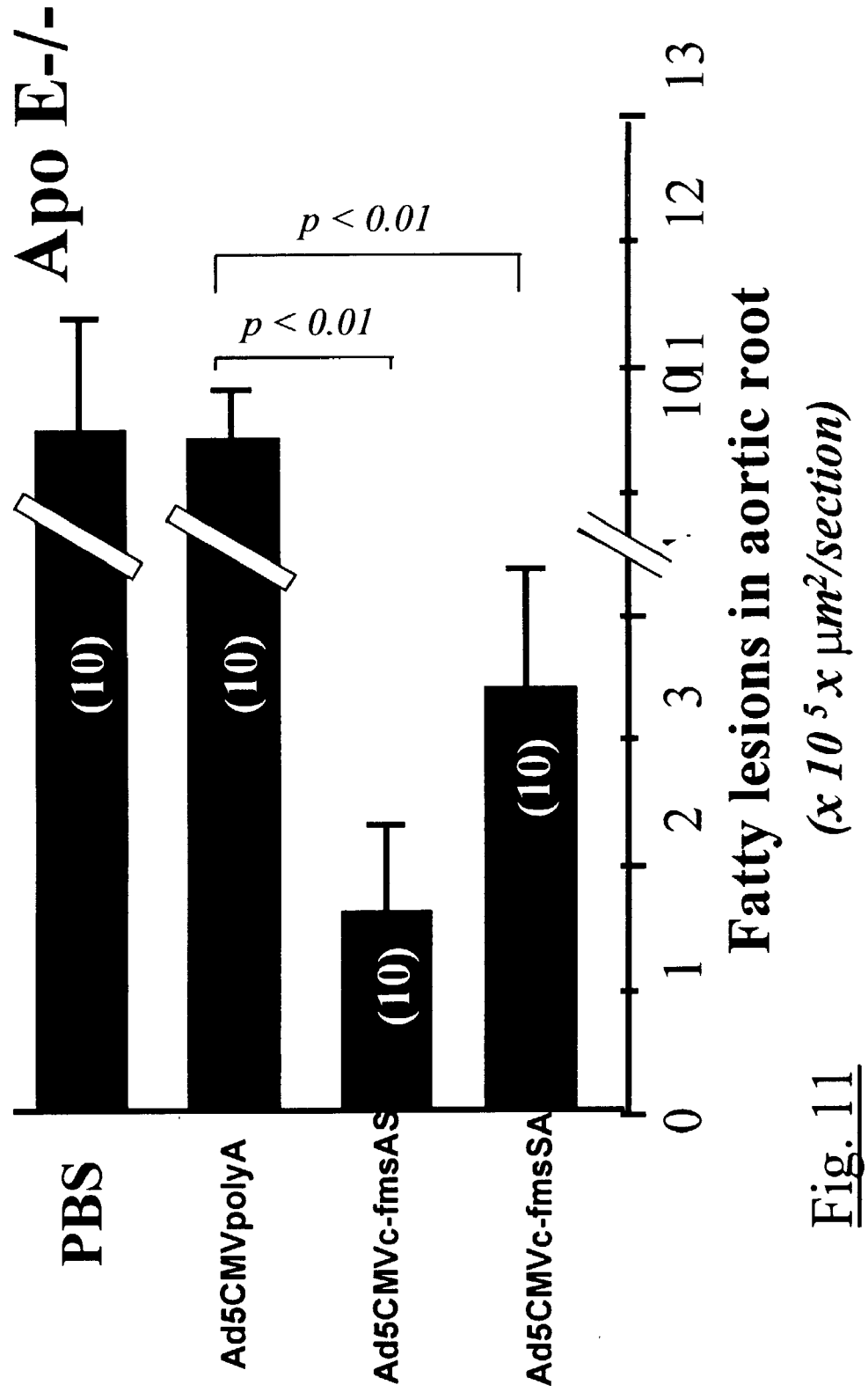
FIG. 11 shows that antisense c-fms RNA markedly inhibits atherosclerosis in apo E-deficient mice.

Results of this experiment indicate that rAd5 mediated transfer of mouse c-fms gene induced expression of antisense c-fms RNA and soluble c-fms in sufficient quantities, for sufficient duration and with sufficient functionality that prevented the progression of atherosclerosis or favourably changed the composition of atherosclerotic plaques (lipid and macrophage depletion) in the apo E-deficient mouse model. A comparison of the outcome of apo E-deficient mice treated with the antisense transgene with that of mice injected with the sequences encoding soluble c-fms revealed that antisense RNA was more potent in providing protection against atherosclerosis (FIG. 10 and 11).

Example 6

Figure 12:
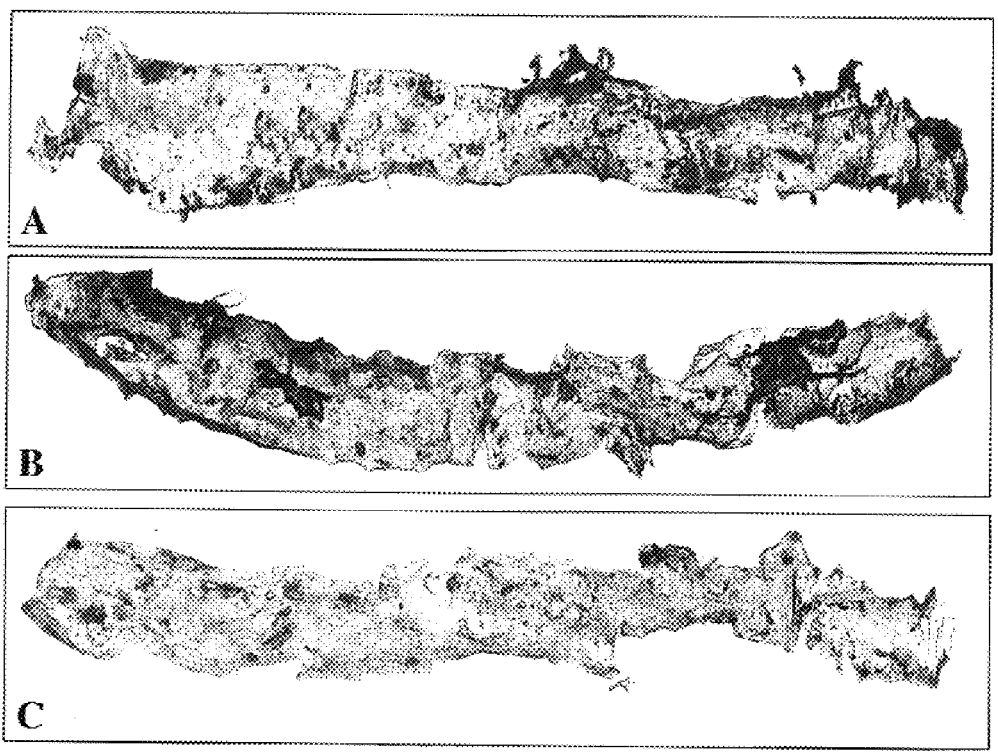
FIGS. 12A–12C (color) show that antisense c-fms RNA markedly inhibits atherosclerosis in LDLR-deficient mice (A depicts a PBS treated mouse; B depicts an Ad5CMVpolyA treated mouse; C depicts an Ad5CMVc-fmsAS treated mouse).

Inhibition of Atherosclerosis by Antisense c-fms RNA Expressed in vivo from Ad5 Vectors in the LDLR-deficient Mouse Model The inventor evaluated the inhibitory effects of antisense cams RNA in vivo in LDLR-deficient mice. Mutant mice fed a high cholesterol diet were given intravenous injections of Ad5CMVc-fmsAS linked to a reporter eGFP gene (1×10e8 pfu in 100 ul volume) beginning at 20 weeks of age with a booster of same dose at 10 days postinjection of Ad5CMVc-fmsAS. Mice were sacrificed five weeks after vector injection. Compared to untreated or vector (Ad5CMVpolyA linked to eGFP reporter) only treated mice, Ad5CMVc-fmsAS -treated mice showed a lack of progression of aortic atherosclerotic lesion despite persistent and marked hypercholesterolemia (FIG. 12). Atherosclerotic lesion area in the aortic arch was 30+5% at the time of vector injection as measured by Oil Red O staining. Lesioned area in mice receiving Ad5CMVpolyA progressed to 52+4% (n=4) whereas lesion size in mice receiving Ad5CMVc-fmsAS was 21+3% ($p<0.05$ vs. rAdGFP, n=4). The antiatherogenic effects of Ad5CMVc-fmsAS were associated with lipid and macrophage depletion from atherosclerotic plaques. There was no evidence of an adverse response with the use of recombinant Ad5CMVc-fmsAS except mild reduction in the number of monocytes. Taken together, these studies indicate that in LDLR null mice, c-fms antisense gene transfer reduces progression of atherosclerosis and favorably alters plaque phenotype despite augmented hypercholesterolemia.

Example 7

Safety of Systemic Administration of rAd5 Expressing Antisense c-fms RNA or Soluble c-fms Protein Histologic examination of areas of injection and various tissues and organs (liver, lung, kidneys, etc.) were performed to detect for the presence of inflammation, necrosis and/or tumor formation. Frozen tissue samples from mice treated with the c-fms sequences encoding either antisense RNA or soluble c-fms well as the control groups were cryostat sectioned at 20 μm thickness and stained with hematoxylin-eosin (H&E). The H&E-stained tissue were examined for the presence of infiltrates.

In order to determine if a humoral immune response may be occurring in animals injected with the recombinant viruses, serum from animals administered with Ad5CMVc-fmsAS, Ad5CMVc-fmsSA and Ad5 vectors were tested for inhibition of cellular transduction in vitro. Using COS or CV-1 cells, serial dilutions of the serum samples were added to their respective recombinant viral particles (rAd5) prior to transduction of the cells. The neutralizing titers of the serum samples were determined by their ability to inhibit transduction in vitro. In order to determine the possible spread of the rAd5 vector to other tissue, tissue samples including gonadal tissue were examined using PCR analysis using specific primers for the antisense c-fms gene.

Example 8

Effect of rAd5-mediated Transfer of Antisense c-fms Transgene on Arterial Response to Injury in the Carotid Injury Model in Apo E-deficient Mice A model of carotid artery injury in the apo E-deficient mouse that results in marked neointimal thickening (S. Oguchi et al., "Increased intimal thickening after arterial injury in hypercholesterolemic apolipoprotein E-deficient mice: finding a novel method," *Circulation*, I-548, 3066 (1997), was used to examine the effects of rAd5-mediated transfer of antisense c-fms transgene on arterial response to injury. The carotid injury was induced by placing a cuff consisting of Tygon tubing around the artery in anesthetized apo E-deficient mice. Three weeks later, substantial neointimal thickening is observed in the segment of carotid artery encased in the cuff. Using this model, the effect of M-CSF deficiency in op/op mice on the neointimal response to injury was previously studied. A total absence of M-CSF was associated with minimal or no neointimal thickening compared to control apo E-deficent mice findings suggesting that M-CSF-mediated cell signalling either directly or indirectly critically contributes to the neointimal response to injury in mice.

Figure 13:
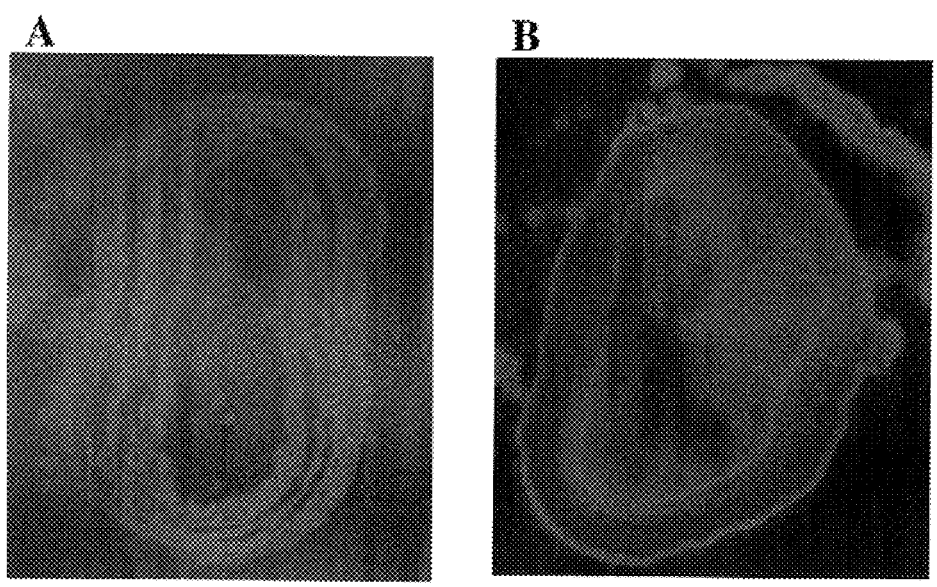
FIGS. 13A and 13B (color) show high levels of expression of a reporter gene following perivascular delivery of the recombinant Ad5 viral vectors (A is gel only; B is gel+$10^9$ pfu/ml Ad5CMVc-fmsAS).
Figure 14:
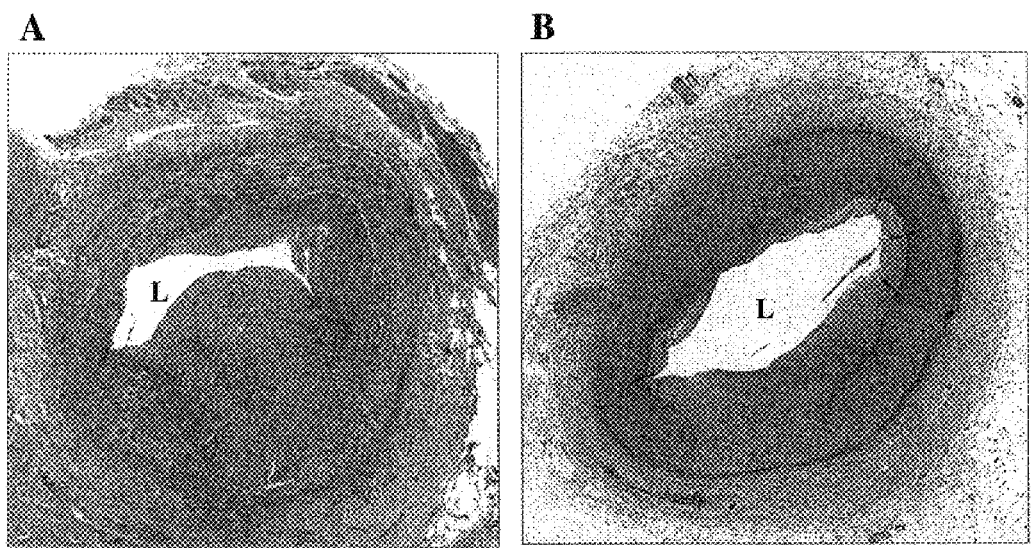
FIGS. 14A and 14B (color) are photographs of porcine coronary artery cross sections intramurally injected either with (A) a vector control (Ad5CMVpolyA), or with (B) a recombinant vector expressing antisense c-fms RNA using the INFILTRATOR®. The INFILTRATOR® is an over-the-wire balloon catheter with 3 lumens; one central lumen for the guidewire, one for balloon inflation, and another for drug infusion. This figure shows exuberant neointimal response in coronary arteries that received control viral vectors and shows appreciable inhibition in the coronary that was injected with viral vectors expressing antisense c-fms RNA.
Figure 15:
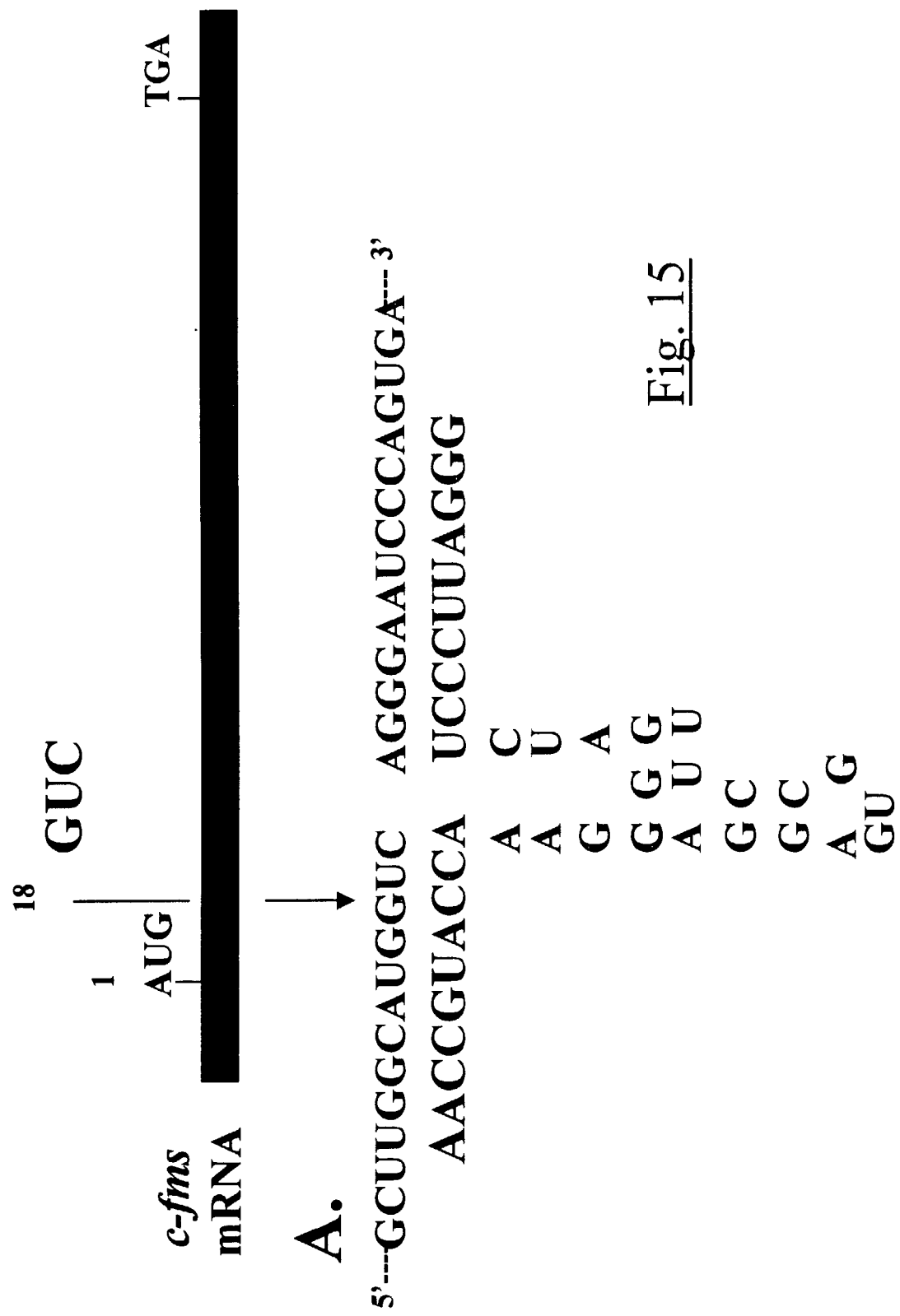
FIG. 15 illustrates a scheme according to one embodiment of the invention to generate hammerhead ribozyme (SEQ ID NO:8) against codon 18 of the c-fms mRNA (SEQ ID NO:7).
Figure 16B:
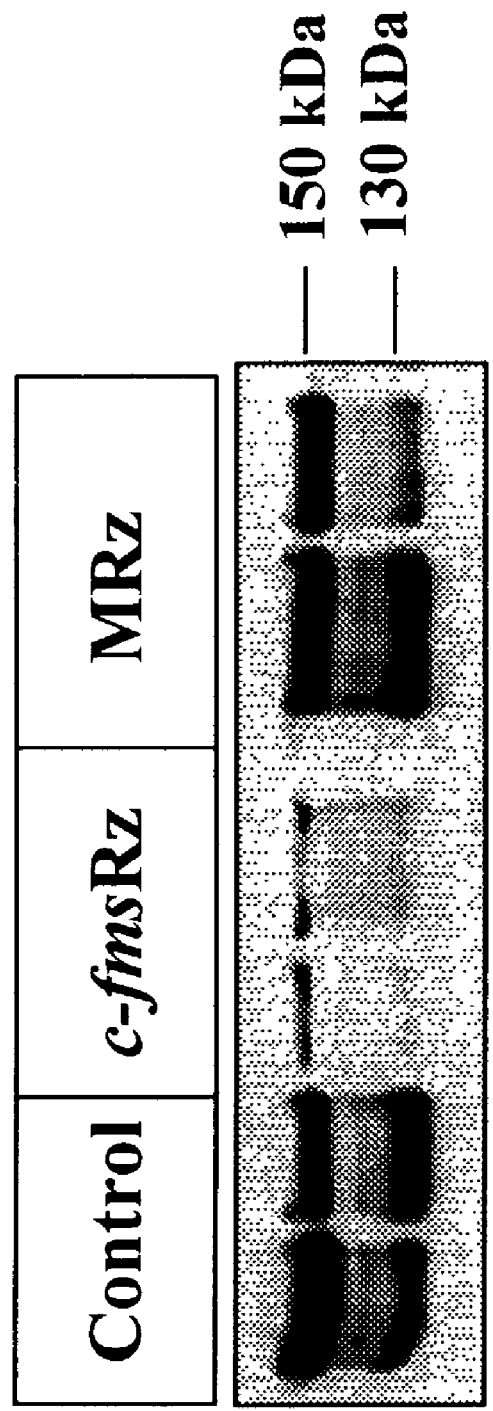
FIG. 16A and B shows that c-fms ribozyme (c-fmsRz) reduces c-fms mRNA and protein levels in cultured mouse macrophage (RAW264.7) cells.
Figure 17:
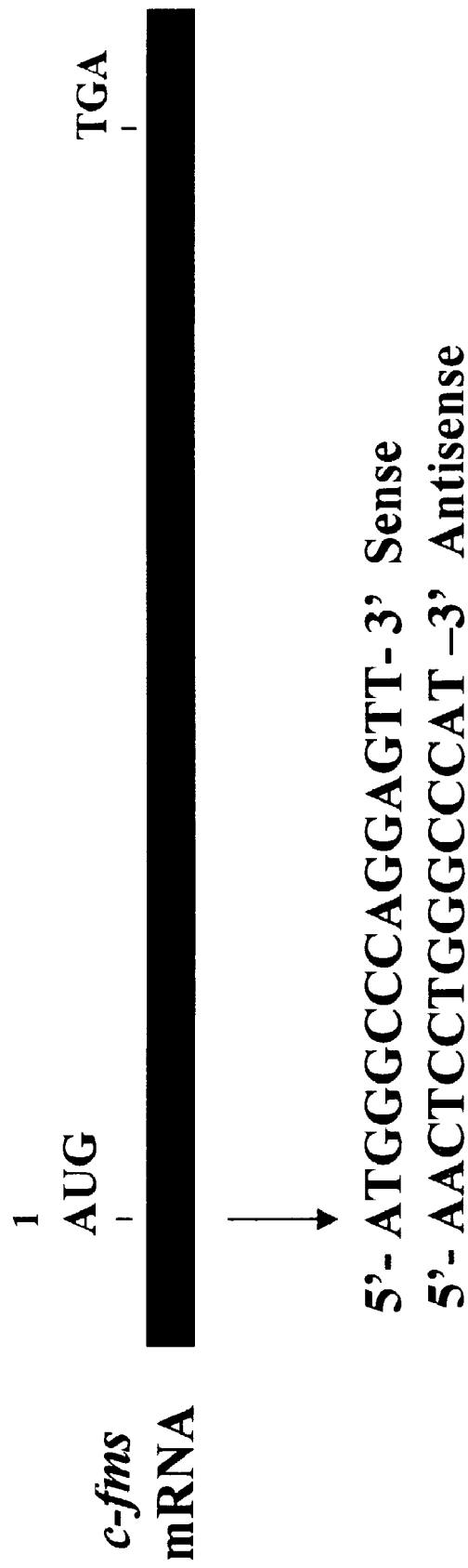
FIG. 17 illustrates two ODN corresponding to the first 15 nucleotides of either sense (SEQ ID NO: 1) or antisense (SEQ ID NO: 2) sequence of the human c-fms mRNA, starting with the initiation codon (AUG). The human c-fms mRNA with the ATG start codon and the TGA stop codon is shown on top.

In order to test critically the vascular effects of antisense c-fms RNA locally in the arterial wall, the inventor used the perivascular delivery system to transduce the carotid artery of apo E-deficient mouse with an Ad5CMVc-fmsAS virus expressing antisense c-fms RNA whose expression was linked to GFP reporter gene. Following the established protocol a dose of Ad5CMVc-fmsAS viral vector containing $5 \times 10^6$ PFU was prepared in 18% (W/W) polymeric gel (dissolved in PBS). The gel with virus was applied to the right carotid artery between the cuff and the vessel. Untreated left carotid in the same animal served as a control. Mice were sacrificed 14 days post transduction and their carotids were processed to visualize GFP. Result of one such experiment is shown in FIG. 13. There was abundant expression of GFP reporter throughout the vessel wall (right panel) in the adenovirus transduced artery as compared to untreated left artery (left panel) indicating local release of viral particles within the arterial wall.

Example 9

Evaluation of the Effects of Local rAd5-mediated Transfer of Antisense c-fms Transgene on Coronary Arterial Luminal Narrowing Response to Balloon-overstretch Injury in Pig M-CSF ligand deficiency in mice exhibits potent vascular antiproliferative properties. rAd5-mediated intramural gene transfer has the potential to provide enhanced delivery efficiency, prolonged recombinant gene expression, and minimization of immune and inflammatory responses. Overexpression of antisense c-fms transgene by intramural delivery system may therefore be a promising method for therapeutic modulation of postinterventional coronary restenosis. An additional advantage is the targeting of the adventitia, which plays a critical role in the coronary arterial response to injury by influencing neointimal formation as well as remodeling.

The subject animals are adult domestic swine weighing 25–30 kgs. Animals are fed a normal diet and housed in a vivarium. After an overnight fast, swine are pretreated with oral aspirin (325 mg) the day prior to coronary artery injury. The animals are immobilized by an IM injection of acepromazine (0.5 mg/kg), ketamine (20 mg/kg), and atropine (0.05 mg/kg), and anesthesia induced with IV thiopental (5–8 mg/kg) and maintained by 1–2% isoflurane after endotracheal intubation. The animals are given bretylium tosylate (250 mg IV) and heparin (5000 U IV) prior to coronary instrumentation. Mechanical ventilation, arterial BP and continuous ECG monitoring is performed throughout the procedure.

Following surgical exposure, an 8F sheath is inserted into the left carotid artery, and an 8F AL-0.75 guiding catheter is advanced to the ostia of the coronary arteries under fluoroscopic guidance. After administration of intracoronary nitroglycerin (200 μg) and angiography to estimate the size of the vessel, balloon injury is performed either on the left anterior descending or the right coronary artery with angioplasty balloons (3.5–4.0 mm in diameter, 20 mm in length) sized so that the ratio of inflated balloon to artery is ~1.3:1. The balloon is inflated to 8–10 atmospheres for 30 seconds three times, with 60 seconds intervals between each inflation. The (ACT-one are then deployed in the other coronary artery in segments averaging 2.7 to 3.0 mm in diameter, using the location of diagonal or septal branches as reference. All stents are hand crimped on a 3.0 mm or 3.5 mm balloon to obtain a final stent:artery ratio of ~1.3:1. The balloon is inflated twice to 6–8 atm for 20–30 seconds to deploy the stent. Angiography is repeated to confirm injury, evidenced by an obvious "step-up" and a "step-down" of the injured segment on visual inspection of the angiogram performed after stent placement.

Following coronary injury, the INFILTRATOR® catheter (InterVentional Technology Inc.) is used for rAd5-mediated gene transfer to the site of injury. The INFILTRATOR® is a triple-lumen balloon catheter allowing intramural drug delivery via 3 longitudinal strips of 6 or 7 low-profile 0.254-mm injector ports capable of penetrating the internal elastic lamina (IEL). The catheter allows local drug delivery without perforation, dissection, or hemorrhage of the arterial segment. The inflation of the 3.08-mm balloon at 2 atm is followed by manual injection of 0.3 mm of the viral solution over a period of 15 seconds. The viral solutions are injected following balloon overstretch injury and prior to stent-implantation injury. The catheters are withdrawn, the carotid artery ligated, and the skin incision closed. As prophylaxis against infection, all animals receive antibiotics at the end of the procedure. The animals are allowed to recover from anesthesia, returned to the vivarium and fed a normal chow diet and aspirin (325 p.o. mg) continued daily until sacrifice, and in addition are given ticlopidine (250 mg p.o. daily) for about 1 wk.

Follow-up coronary angiography and intravascular ultrasonography (IVUS) are obtained at specific time intervals (as described in the experimental protocol), following which animals are euthanized by an overdose of pentobarbital (50 mg/kg IV) under general anesthesia. The heart is excised after thoracotomy, and the coronary arteries are perfused first with saline to clear the blood, then perfusion-fixed with 2% paraformaldehyde for 15 minutes followed by immersion in 4% paraformaldehyde in phosphate buffer (pH 7.4) for 4 hours, and then stored in 70% ethanol. To preserve the integrity of the adventitial and perivascular tissues, coronary arteries are carefully removed along with adjacent tissues (the surrounding adipose tissue and myocardium). The arteries are sectioned into 3-mm blocks from three segments (proximal, middle and distal) of the injured portion of each artery, embedded in paraffin, cut into 15 μm-thick sections, and then stained with hemotoxylin and eosin, and elastin stain for histomorphometric analysis. For stented segments, special histologic processing is performed to maintain the vascular architecture with the metallic stent struts intact. Tissue blocks are cut with a diamond wafering blade and embedded in methyl methacrylate. Two radial cross sections containing 12 struts are cut; one from the proximal and one from the distal half of each stent. Sections are ground to a thickness of about 50 μm, optically polished, and stained with toluidine blue (paragon stain).

Quantitative coronary angiography (QCA) is used to assess minimum luminal diameter (MLD) at specific time points (pre-injury, immediately post-injury, and 28 days following injury immediately prior to euthanasia. Late luminal loss is calculated as the difference in the mean luminal diameter (MLD) immediately post-balloon injury and at 28 days following injury. Remodeling index is calculated as late luminal loss divided by post-injury MLD. Percent stenosis of the injured segments is also estimated using the uninjured segments as reference. The following (IVUS) parameters are measured: stent area, intimal area, % area stenosis, luminal loss, and % diameter stenosis.

A computerized imaging system (Optimas) is used for histomorphometric measurements of: 1) mean cross-sectional area and thickness of lumen (area circumscribed by the intima/neointima-luminal border); neointima (area between the lumen and the IEL, and when the IEL is missing, the area between the lumen and the remnants of media or the external elastic lamina [EEL]); media (area between the IEL and the EEL); vessel size (area circumscribed by the EEL but excluding the adventitial area); adventitia (area between the periadventitial tissues, adipose tissue and myocardium, and the EEL); and 2) Injury score. To quantify the degree of vascular injury, a score based on the amount and length of tear of the different wall structures is used. The degree of injury is calculated as follows: 0—intact IEL; 1—ruptured IEL with exposure to superficial medial layers; 2—ruptured IEL with exposure to deeper medial layers (medial dissection); 3—ruptured EEL with exposure to the adventitia. The injury score for each of the three segments is averaged to obtain the mean artery injury score. The circumference of the IEL and the length of its rupture, when present, are measured, as are minimal and maximal thicknesses of the neointima, media and adventitia. The relationship between the neointimal and adventitial responses, luminal dimensions, and the extent of injury will also be plotted.

The Vectastain Elite ABC system (Vector Laboratories) will be used for immunohistochemistry to identify proliferating cell nuclear antigen (PCNA) to assay the degree of S-phase activity and macrophage infiltration. Cell density and cell proliferation index is determined by counting total cell nuclei and PCNA-positive nuclear staining, respectively, in a minimum of 200–300 cells per vessel layer per field. Cellularity is expressed as number of cells per $mm^2$, and proliferation index as percentage of PCNA-positive cells. Macrophage content is quantified as macrophage-stained area as a percent of total neointimal area.

In vivo, soluble c-fms expression is evaluated by immunohistochemistry on frozen arterial sections. Coronary arterial rings of swine infected with rAd5-soluble c-fms is harvested on day 7 (immunocytochemistry protocol) or day 28 (histomorphometry protocol). Sections are incubated overnight with a monoclonal mouse anti-human soluble c-fms IgG antibody, followed by incubation with polyclonal goat anti-human soluble c-fms IgG for 30 minutes in phosphate buffer containing 1% $H_2O_2$. Biotinylated rabbit anti-mouse antibody is used as a secondary antibody (Vector Laboratories Inc), and antibody binding is visualized by the avidin-biotin complex method (ABC kit, Vector Laboratories, Inc). For cell-type identification, antibodies specific to SMC α-actin (Boehringer), endothelial cell von Willebrand factor (DAKO), and macrophage CD68 antigen (DAKO) are applied to adjacent sections. Primary antibodies are localized with appropriate Biotinylated secondary antibodies and tertiary avidin-biotin-complex staining (Vector Laboratories). Sections are counterstained with hematoxylin or methyl green and examined by light microscopy.

The following is used to assess gene transfer efficiency. Irrelevant rAd5-placental alkaline phosphatase (PLAP) gene transfer (0.3 ml of $10^{11}$ infectious units/ml), using the CMV and U1 promoter, is performed via the INFILTRATOR® catheter in native uninjured and balloon-injured arteries (in the same animal) at day 0. Animals are euthanized on day 7 (n=3 each), 14 (n=4 each), and 28 (n=3 each), and the coronary arteries are cannulated, perfused with 4% formaldehyde at 100 cm $H_2O$ pressure for 2 hours, and washed with PBS for 24 hours. To identify transduced cells expressing the transgene, arteries are cut into 5-mm rings and prepared for alkaline phosphatase histochemical analysis using previously described methods. The entire vessel length will be scanned, and the medial and adventitial cells expressing the transgene are identified by positive stain for PLAP.

The following experimental groups are studied: 1) Histomorphometry (day 28): 0.3 ml of $10^9$ and $10^{11}$ infectious units/ml of rAd5-soluble c-fms (8 balloon-injured and 8 stent-injured arteries each for each of the two doses, n=16 total arteries); 0.3 ml of $10^9$ and $10^{11}$ infectious units/ml of rAd5-soluble c-fms$_{wt}$ (n=16); and 0.3 ml of $10^{11}$ infectious units/ml of rAd5-control (n=8). The total number of animals studied in this group will be 40. 2) Immunocytochemistry (day 7): 0.3 ml of $10^{11}$ infectious units/ml of rAd5-soluble c-fms (5 balloon-injured and 5 stent-injured arteries, n=5 arteries total); 0.3 ml of $10^{11}$ infectious units/ml of rAd5-soluble c-fms (n=5); and 0.3 ml of $10^{11}$ infectious units/ml of rAd5-control (n=5). The total number of animals studied in this group is 15. The total number of animals studied =75; the total amount of rAd5 required for these studies is 12 ml of $10^{12}$ infectious particles per ml.

Following baseline angiography, each animal undergoes balloon overstretch injury in one coronary artery (right coronary artery [RCA] or LAD) and stent implantation injury in the other artery in a randomized fashion. Thus, the relative impact of remodeling and hyperplasia on vascular response to injury is examined in the same animal but in different arteries. Unlike the balloon overstretch model where there is a wide variation in vascular injury, the stent overinflation model is a more robust model because the injury is more severe but consistent, resulting in a more exuberant proliferative response and greater associated neointimal formation. Following injury, each artery is infiltrated with the active gene or a control infusate. The animals are euthanized at day 28 after an angiogram and IVUS, and tissues prepared for histomorphometric analysis. In some animals, immunohistochemistry for PCNA and macrophage infiltration is performed at day 7, as cell proliferation and inflammation peak around this time in this model.

What is claimed is:

1. A method of inhibiting macrophage colony stimulating factor (M-CSF), the method comprising:
   providing a recombinant viral vector comprising a nucleic acid expressing antisense c-fms RNA; and
   administering the recombinant viral vector to a mammal in an amount effective to inhibit the M-CSF by an administration technique selected from the group consisting of intramural delivery, delivery with a nipple balloon catheter, periadventitial delivery, and inclusion in a coating on a stent that is implanted in the mammal, wherein the nucleic acid is constructed using at least one primer selected from the group consisting of a primer represented by SEQ ID NO:5, a primer represented by SEQ ID NO:6, and combinations thereof, and the nucleic acid corresponds to the ligand binding domain of a c-fms receptor.

2. The method of claim 1, wherein administering the recombinant viral vector further comprises administering the vector to a mammal with a vascular disease in an amount effective to inhibit the vascular disease.

3. The method of claim 2, wherein the vascular disease is selected from the group consisting of atherosclerosis, angina, myocardial infarction, stroke, transient ischemic attacks, osteonecrosis, ischemic colitis, peripheral vascular disease, claudication, renal disease, congestive heart failure, and complications of diabetes.

4. The method of claim 1, wherein the nucleic acid is operatively associated with a promoter.

5. The method of claim 4, wherein the promoter is selected from the group consisting of U1, CMV, and combinations thereof.

6. The method of claim 4, wherein the promoter is a tissue-specific promoter.

7. The method of claim 1, wherein the recombinant viral vector is administered at a dose of from about $1 \times 10^8$ to about $5 \times 10^{16}$ viral vector genomes per mammal.

8. The method of claim 1, wherein the mammal is a human.

9. The method of claim 2, wherein the vascular disease is restenosis following a procedure to reduce atherosclerosis.

10. The method of claim 9, wherein the procedure is selected from the group consisting of angioplasty and balloon angioplasty.

11. The method of claim 1, wherein the viral vector is selected from the group consisting of an adenovirus, an adeno-associated virus, a retrovirus, and a lentivirus.

* * * * *

SEQUENCE LISTING

<160> NUMBER OF SEQ ID NOS: 8

<210> SEQ ID NO 1
<211> LENGTH: 15
<212> TYPE: DNA
<213> ORGANISM: Unknown
<220> FEATURE:
<223> OTHER INFORMATION: ODN

<400> SEQUENCE: 1
atgggcccag gagtt                                                    15

```
<210> SEQ ID NO 2
<211> LENGTH: 15
<212> TYPE: DNA
<213> ORGANISM: Unknown
<220> FEATURE:
<223> OTHER INFORMATION: ODN

<400> SEQUENCE: 2
aactcctggg cccat                                                       15

<210> SEQ ID NO 3
<211> LENGTH: 15
<212> TYPE: DNA
<213> ORGANISM: Unknown
<220> FEATURE:
<223> OTHER INFORMATION: ODN

<400> SEQUENCE: 3
agcggccctg gagta                                                       15

<210> SEQ ID NO 4
<211> LENGTH: 16
<212> TYPE: DNA
<213> ORGANISM: Unknown
<220> FEATURE:
<223> OTHER INFORMATION: ODN

<400> SEQUENCE: 4
tgactcatgc gggccc                                                      16

<210> SEQ ID NO 5
<211> LENGTH: 37
<212> TYPE: DNA
<213> ORGANISM: Unknown
<220> FEATURE:
<223> OTHER INFORMATION: Primer

<400> SEQUENCE: 5
ggatccgcta gctataaata tggagttggg gcctcct                                37

<210> SEQ ID NO 6
<211> LENGTH: 36
<212> TYPE: DNA
<213> ORGANISM: Unknown
<220> FEATURE:
<223> OTHER INFORMATION: Primer

<400> SEQUENCE: 6
gggttaactc gagctagctc actgcaagag gctctg                                 36

<210> SEQ ID NO 7
<211> LENGTH: 28
<212> TYPE: RNA
<213> ORGANISM: Unknown
<220> FEATURE:
<223> OTHER INFORMATION: c-fms RNA

<400> SEQUENCE: 7
gcuuggcaug gucagggaau cccaguga                                          28

<210> SEQ ID NO 8
<211> LENGTH: 42
<212> TYPE: RNA
<213> ORGANISM: Unknown
<220> FEATURE:
```

```
-continued

<223> OTHER INFORMATION: Ribozyme

<400> SEQUENCE: 8
gggauucccu cugaaguguc cgugaggacg aaaccaugcc aa                    42
```